United States Patent [19]
O'Neill et al.

[11] Patent Number: 6,124,092
[45] Date of Patent: Sep. 26, 2000

[54] MULTIPLEX POLYNUCLEOTIDE CAPTURE METHODS AND COMPOSITIONS

[75] Inventors: Roger A. O'Neill, San Carlos; Jer-Kang Chen, Palo Alto; Claudia Chiesa, Foster City; George Fry, San Carlos, all of Calif.

[73] Assignee: The Perkin-Elmer Corporation, Foster City, Calif.

[21] Appl. No.: 08/873,437

[22] Filed: Jun. 12, 1997

Related U.S. Application Data

[60] Provisional application No. 60/027,832, Oct. 4, 1996.

[51] Int. Cl.[7] .............................. C12Q 1/68; C12P 19/34; C07H 21/02; C07H 21/04
[52] U.S. Cl. ......................... 435/6; 435/91.2; 536/23.1; 536/24.3; 935/76; 935/77; 935/78
[58] Field of Search ............................... 436/6; 435/91.2; 536/23.1, 24.3; 935/76, 77, 78

[56] References Cited

U.S. PATENT DOCUMENTS

| | | |
|---|---|---|
| 4,942,124 | 7/1990 | Church . |
| 5,112,736 | 5/1992 | Caldwell et al. . |
| 5,149,625 | 9/1992 | Church et al. ............... 435/6 |
| 5,200,314 | 4/1993 | Urdea ........................... 435/6 |
| 5,470,710 | 11/1995 | Weiss et al. . |
| 5,514,256 | 5/1996 | Douthart et al. . |
| 5,552,278 | 9/1996 | Brenner et al. . |
| 5,582,989 | 12/1996 | Caskey et al. ............... 435/6 |
| 5,624,825 | 4/1997 | Walker et al. . |
| 5,695,934 | 12/1997 | Brenner ....................... 435/6 |
| 5,714,318 | 2/1998 | Sagner et al. ................ 435/6 |
| 5,763,175 | 6/1998 | Brenner ....................... 435/6 |
| 5,846,719 | 12/1998 | Brenner et al. . |
| 5,935,793 | 8/1999 | Wong .......................... 435/6 |

FOREIGN PATENT DOCUMENTS

| | | |
|---|---|---|
| 0 416 817 | 3/1991 | European Pat. Off. .......... C12Q 1/68 |
| 416817A2 | 3/1991 | European Pat. Off. . |
| WO 94/02634 | 2/1994 | WIPO .............................. C12Q 1/68 |
| WO 94/11529 | 5/1994 | WIPO .............................. C12Q 1/68 |
| WO 94/21820 | 9/1994 | WIPO .............................. C12Q 1/68 |
| WO 95/35505 | 12/1995 | WIPO ......................... G01N 33/543 |
| WO 96/02836 | 2/1996 | WIPO ......................... G01N 33/543 |
| WO 96/27025 | 9/1996 | WIPO .............................. C12Q 1/68 |
| WO 96/36737 | 11/1996 | WIPO .............................. C12Q 1/68 |
| WO 97/07245 | 2/1997 | WIPO .............................. C12Q 1/68 |

OTHER PUBLICATIONS

Kretz et al., "Cycle Sequencing", PCR Methods and Applications 3 : S107–S112 (1994).

Gade et al., "Incorporation of Nonbase Residues into Synthetic Oligonucleotides and their use in the PCR", GATA 10(2) : 61–65 (1993).

Church et al., "Multiplex DNA Sequencing," *Science* 240:185–188 (1988).

Yang et al., "A Prospectus for Multispectral–Multiplex DNA Sequencing," *Nature Bio/Technology* 7:576–580 (1989).

Patrick M. Gillevet, "Chemiluminescent Multiplex DNA Sequencing," *Nature* 348:657–658 (1990).

Mark Chee, "Enzymatic Multiplex DNA Sequencing," *Nucleic Acids Research* 19(12):3301–3305 (1991).

*Primary Examiner*—W. Gary Jones
*Assistant Examiner*—Ethan Whisenant
*Attorney, Agent, or Firm*—Scott R. Bortner

[57] ABSTRACT

The invention relates to methods and compositions for simultaneously generating a plurality of polynucleotide sequencing ladders or PCR amplification products. Each sequencing ladder is generated from a recoverable primer, i.e., an oligonucleotide primer comprising a recovery tag. The recovery tag may be an oligonucleotide. Each sequencing ladder has a unique recovery tag. After the generation of the multiple sequencing ladders, the different sequencing ladders are separated from one another, i.e., purified, by binding to recovery tag binding compounds that have been immobilized on one or more solid supports. The recovery tag binding compounds are immobilized on the solid support in an addressable manner, i.e., the recovery tag binding compounds have distinct locations on the solid support. The binding of the sequencing ladders to the recovery tag binding compounds serves to separate the different polynucleotide sequencing ladders present in a given solution. The separated sequencing ladders may then be released from the immobilized recovery tag binding compounds and subsequently resolved into individual components of the sequencing ladders or PCR products. The subject methods of separating sequencing ladders simultaneously generated in the same vessel may readily be adapted to separate a plurality of simultaneously generated polynucleotide amplification products. Other aspects of the invention are kits for the generation or recovery of a plurality of polynucleotide sequencing ladders or amplification products. The kits comprise a plurality of recoverable primers having unique recovery tags. Preferably, the recovery tags are polynucleotides that have substantially the same denaturation temperature when bound to appropriate recovery tag binding compounds, i.e., the primers comprise an integrated set. The kits may further comprise recovery tag binding compounds. The kits may further comprise labeled chain terminators. Other aspects of the invention include polynucleotide recovery devices.

17 Claims, 4 Drawing Sheets

MULTIPLEX POLYNUCLEOTIDE CAPTURE METHODS AND COMPOSITIONS

RELATED APPLICATIONS

This application is a continuation-in-part of provisional application 60/027,832 filed Oct. 4, 1996.

FIELD OF THE INVENTION

This invention is in the field of polynucleotide sequencing and amplification.

BACKGROUND

The sequencing of polynucleotides is a well established technique in molecular biology. Currently used procedures for sequencing are essentially as described in Sanger et al, *Proc. Natl. Acad. Sci. USA* 74:5463–5467 (1977) or Maxam et al., *Methods in Enzymology* 65:499–559, Academic Press, San Diego, Calif. (1980). Polynucleotide sequencing has become integral to virtually all aspects of molecular genetics. The Human Genome Project, and the sequencing of entire genomes from a variety of organisms has put great pressure on those researchers using conventional sequencing techniques. Additionally, the comparative sequencing of known genes for diagnostic purposes is expected to become increasingly important.

The amplification of polynucleotide sequences, typically through techniques such as PCR (polymerase chain reaction) is also a well established technique in molecular biology. The need for increased numbers of amplification reactions for genetic analysis, driven in part by the increased need for sequencing, has increased the need to perform large numbers of polynulceotide amplifications.

Given that the need for polynucleotide sequencing is rapidly increasing, there is ever growing pressure to reduce the time and costs associated with obtaining polynucleotide sequences. Many attempts have been made to perform sequencing in parallel, i.e., multiplex DNA sequencing. Methods of multiplex sequencing have been described in PCT application PUT/US96/09513, and U.S. Pat. No. 5,149,625. These techniques are either difficult to carry out, produce small amounts of sequence information, or do not provide significant savings of time or money. Similarly, established methods of multiplex PCR, e.g., as described in U.S. Pat. No. 5,582,989, are difficult to carry out on a large scale.

Conventional sequencing methods are impractical for high throughput sequencing because of numerous reasons such as the cost of reagents and the large number of sample handling steps required. Similarly, conventional polynucleotide amplification methods are impractical for high throughput sequencing for numerous reasons such as the cost of reagents and the large number of sample handling steps required. The inventions described herein may be used to both increase the amount of genetic information obtained in a given period of time and to decrease the costs of obtaining the genetic information.

BRIEF DESCRIPTION OF THE DRAWINGS

In FIG. 1A, the recoverable primer has a balancing sequence and the recovery tag binding compound hybridizes the balancing sequence. In FIG. 1B, the recoverable primer has a balancing sequence and the recovery tag binding compound hybridizes to the balancing sequence and to the template-annealing region of the recoverable primer. In FIG. 1C, the recoverable primer does not have a balancing sequence and the recovery tag binding compound hybridizes to the template-annealing region of the recoverable primer. In FIG. 1D, the recoverable primer does not have a balancing sequence. Newly synthesized DNA is depicted by bold italicized letters, and the recovery tag binding compound hybridizes to a template-annealing region of the recoverable primer and to the newly synthesized DNA strand. In FIG. 1E, the recoverable primer does not have a balancing sequence. Newly synthesized DNA is depicted by bold italicized letters, and the recovery tag binding compound hybridizes to the newly synthesized DNA strand.

SUMMARY OF THE INVENTION

Figure 1:
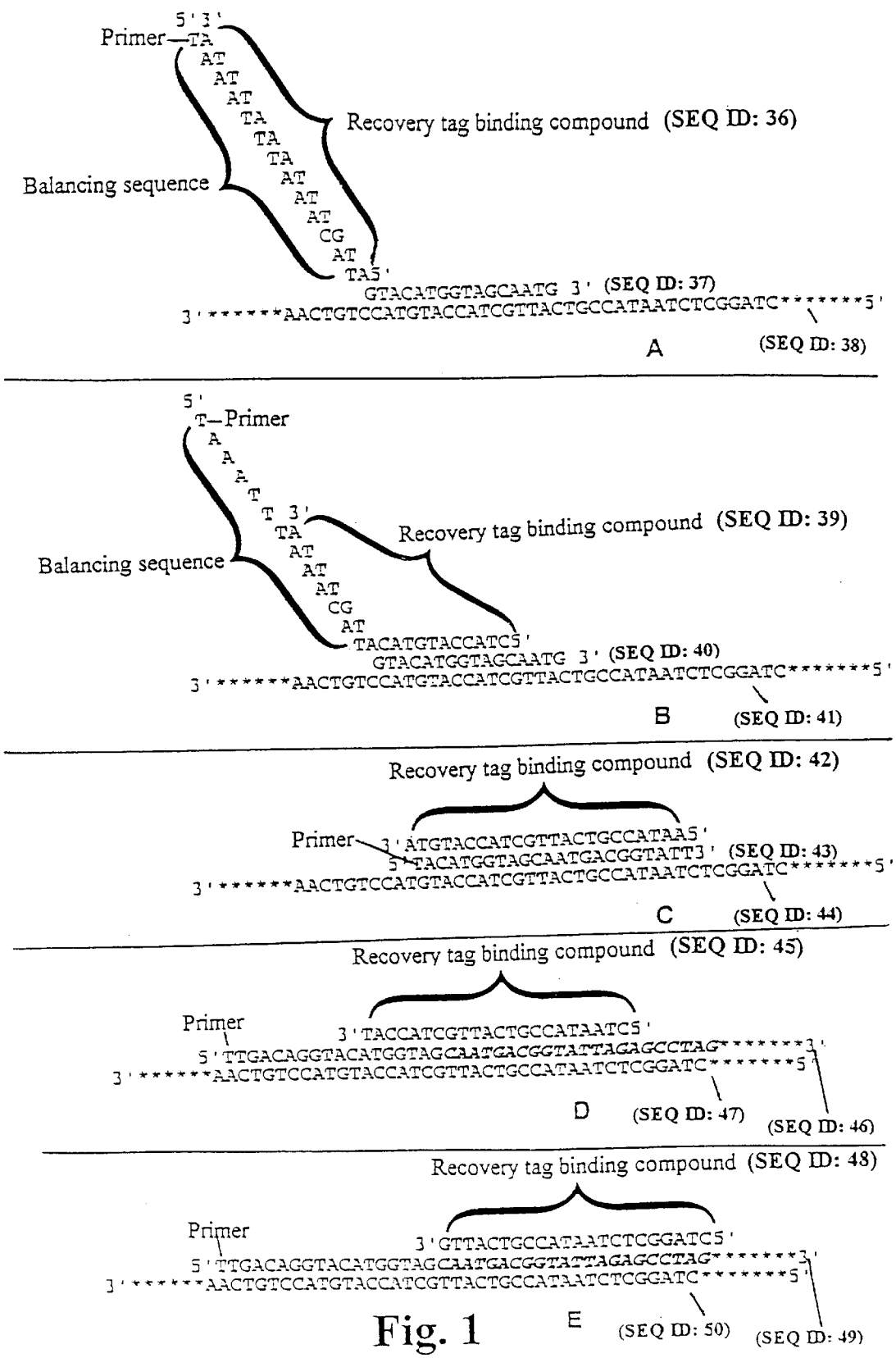
FIG. 1. This figure is a schematic representation of examples of different embodiments of pairs of recoverable primers and recovery tag binding compounds. The recovery tags and the recovery tag binding compounds are both polynucleotide sequences. The sequences are aligned to show orientation and should not be construed as representing triplex sequences. Conventional duplex A-T and C-G pairing is represented. The asterisks represent unspecified bases in the template.
Figure 2:
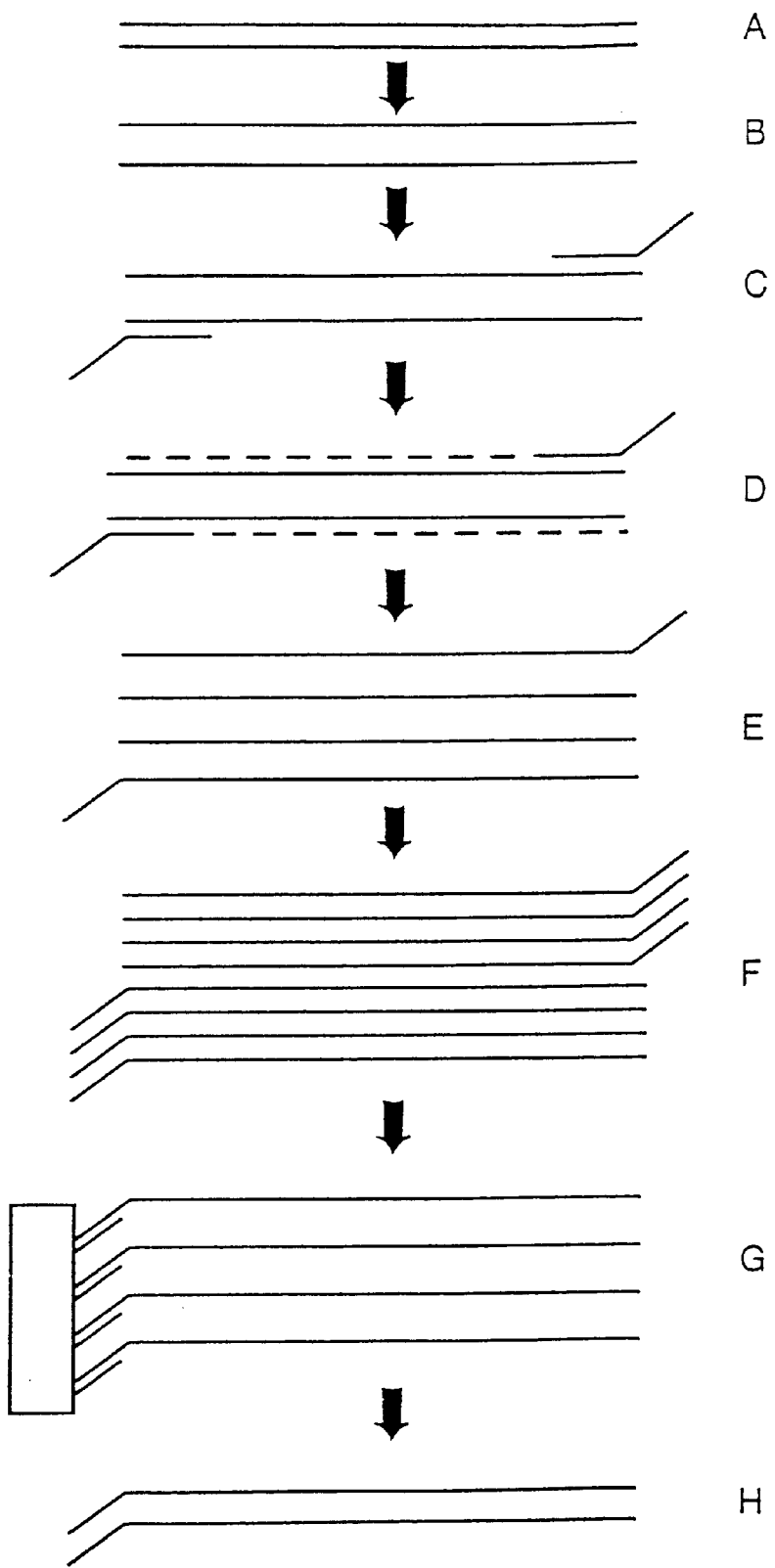
FIG. 2. This figure is a schematic representation of an embodiment of the invention for multiplex polynucleotide amplification. 2A shows double stranded DNA. 2B shows denatured DNA. 2C shows two recoverable amplification primers annealed to the denatured DNA templates. The recoverable primers have recovery tags that do not anneal to the template. 2D shows primer extensions from the annealed recoverable primers. 2E shows a denaturation step in PCR. 2F shows the net result of repeated rounds of amplification. 2G shows one of the amplification product strands bound to a recovery tag binding compound. The recovery tag binding compounds are bound to a solid support (represented by a rectangle). The recovery tag binding compounds are represented by the short lines attached to the solid support. 2H shows the purified amplified DNA after release (denaturation) from the solid support.

The invention relates to methods and compositions for simultaneously generating a plurality of sequencing ladders (or other polynucleotide extension products), typically in a single reaction vessel and analyzing the simultaneously generated sequencing ladders. Each sequencing ladder is generated from a recoverable primer, i.e., an oligonucleotide primer comprising a recovery tag that may be used to purify or concentrate an individual sequencing ladder. Alternatively, functional equivalents to recovery tags may be used instead of recovery tags. Preferably, the recovery tags are oligonucleotides. Each sequencing ladder is characterized by a unique recovery tag that was originally present on the recoverable primer. After the generation of the multiple sequencing ladders, the different polynucleotide sequencing ladders are separated from one another, i.e., purified, by binding to recovery tag binding compounds that have been immobilized on one or more solid supports. Recovery tag binding compounds are compounds that specifically bind to recovery tags. Preferably, recovery tag binding compounds are oligonucleotides that are complementary to oligonucleotide recovery tags. Recovery tag binding compounds are immobilized on the solid support in an addressable manner, e.g., the recovery tag binding compounds have distinct locations on the solid support or may be located by referring to a specific solid support. The binding of the polynucleotide sequencing ladders to the recovery tag binding compounds serves to separate the different polynucleotide sequencing ladders present in a given solution. The separated polynucleotide sequencing ladders may then be released from the solid support and subsequently resolved into the individual components, i.e., polynucleotides, of the sequencing ladders. The methods of the invention are especially useful when used in conjunction with automated fluorescence based sequencing apparatus. The recoverable primers may be fluorescently labeled for use in such apparatus. The templates for sequencing by the subject sequencing methods may be polynucleotide amplification products. The sequencing ladders may be generated by a variety of DNA sequencing techniques, including cycle sequencing.

Another aspect of the invention is to provide methods and compositions for separating a plurality of simultaneously generated polynucleotide amplification products, such as the amplification products produced by multiplex PCR. In the subject methods of separating a plurality of simultaneously generated polynucleotide amplification products, each amplification product is formed from at least one recoverable primer having a unique recovery tag (or the functional equivalent of a recovery tag). In other embodiments of the invention, the same recovery tag may be present on the different amplification products so as to provide for the purification of distinct sets of amplification products.

After the generation of amplification products, the different amplification products are separated from one another by binding to recovery tag binding compounds that have been immobilized on one or more solid supports. The recovery tag binding compounds are immobilized on the solid support in an addressable manner. The binding of the amplification products to the recovery tag binding compounds serves to separate, purify, or concentrate the different polynucleotide amplification products. The separated polynucleotide amplification products may then be released from the solid support and subsequently resolved, e.g., separated by electrophoresis. The invention also includes methods that combine the subject multiplex sequencing and multiplex nucleic acid amplification techniques.

Another aspect of the invention is to provide recoverable primers that have as a recovery tag, an oligonucleotide that cannot be replicated during an amplification reaction. Such recoverable primers are referred to herein as "hinged primers." Example of hinged primers include recoverable primers that comprise an abasic region between the template-annealing region of the primer and the recovery tag. Another example of a hinged primer is a recoverable primer that comprises peptide-nucleic acid (PNA) as a recovery tag, wherein the PNA is joined to the 5' end of the template-annealing region of the primer. The recovery tag oligonucleotides of hinged primers may also be rendered incapable of replication during an amplification reaction by joining the recovery tag oligonucleotide to the primer by means of non replicable linkers. Hinged primers are particularly useful for multiplex polynucleotide amplification reactions because there is no need to denature (and thus prevent from renaturing) a double-stranded polynucleotide comprising the recovery tag oligonucleotide. The invention also provides methods of using hinged primers in multiplexed polynucleotide amplification reactions.

Other aspects of the invention are kits for the generation or recovery of a plurality of polynucleotide sequencing ladders or amplification products. The kits comprise a plurality of recoverable primers having unique recovery tags. The recoverable primers may be supplied in a single solution. Preferably, the recovery tags are polynucleotides that have substantially the same denaturation temperature when bound to appropriate recovery tag binding compounds, i.e., the primers form an integrated set. The kits may further comprise recovery tag binding compounds. The recovery tag binding compounds are preferably supplied immobilized to solid supports in a addressable manner. The kits may further comprise labeled chain terminators, DNA polymerases, pyrophosphatases, unlabeled chain terminators, DNA polymerase, pyrophosphatase or other components required for PCR or sequencing reactions.

Other aspects of the invention include sets of sequencing or amplification primers that are optimized for use in the methods of the invention. Examples of such sets of primers are sets of recoverable sequencing primers that may be released from recovery tag binding compounds under similar denaturation conditions. The primers included in such sets may be hinged or not hinged.

Other aspects of the invention include polynucleotide recovery devices. Such devices may be used in the methods of the invention. The polynucleotide recovery devices comprise a plurality of recovery tag binding compounds immobilized, in some embodiments, in a spatially addressable manner to one or more solid supports. Preferably, the recovery tag binding compounds are polynucleotides. In one embodiment of the subject devices, the solid support is an array of capillary channels. In other embodiments of the invention, the solid support may also take the form of beads or a multiple-projection electrophoresis loading device (e.g., a gel comb), or other multiple-projection devices for handling samples.

DESCRIPTION OF THE SPECIFIC EMBODIMENTS

Definitions

The terms "polynucleotide" and "oligonucleotide" as used herein are used broadly to include naturally occurring polynucleotides, e.g., DNA or RNA, and to also include analogs of naturally occurring polynucleotides. Such analogs include, but are not limited to, phosphoramidates, peptide-nucleic acids, phosphorothioates, methylphosphonates, and the like. In addition to having non-naturally occurring backbones, analogs of naturally occurring polynucleotides may comprise nucleic base analogs, e.g., 7-deazaguanosine, 5-methyl cytosine, inosine, and the like. Descriptions of how to synthesize polynucleotides can be found, among other places, in U.S. Pat. Nos. 4,373,071; 4,401,796; 4,415,732; 4,458,066; 4,500,707; 4,668,777; 4,973,679; 5,047,524; 5,132,418; 5,153,319; and 5,262,530.

The term "sequencing ladder" as used herein refers to a set of polynucleotides that is produced from a sequencing reaction, either a chain termination sequencing reaction, e.g., dideoxy sequencing, or from chemical cleavage sequencing, e.g., Maxam and Gilbert sequencing. The process of producing a sequencing ladder is referred to herein as "sequencing ladder generation" or "generating a sequence ladder." Methods for generating polynucleotide sequencing ladders are well known to persons of ordinary skill in the art. Examples of methods of generating a sequencing ladder can be found, among other places, in Sambrook et al, *Molecular Cloning Methods: A Laboratory Manual* Coldspring Harbor, Coldspring Harbor Press (1989). The different polynucleotides, i.e., members, of a specific sequencing ladder, differ in length from one another, but all members of the same ladder comprise the same oligonucleotide primer from which that sequencing ladder is derived. Thus, generating sequencing ladders from a first recoverable primer and a second recoverable primer that anneal to the same template priming site, but differ with respect to the identity of the recovery tags, are said to result in the synthesis of two different sequencing ladders. In addition to being derived from the same primer, the members of a given polynucleotide sequencing ladder are also derived from the same sequencing template. In labeled primer sequencing, four different sequencing ladders, each using a different dideoxy terminating base are generated separately (and may subsequently be combined prior to analysis), even though only a single completed sequence is obtained from combining the information in the four constituent sequencing ladders. When the same recoverable sequencing primer and template are used to generate sequencing ladders in separate reaction vessels, the sequencing ladders produced are said to be different sequencing ladders.

The term "specific binding pair" refers to a pair of molecules that specifically bind to one another. Binding between members of a specific binding pair is usually non-covalent. Examples of specific binding pairs include, but are not limited to antibody-antigen (or hapten) pairs, ligand-receptor pairs, biotin-avidin pairs, polynucleotides with complementary base pairs, and the like. Each specific binding pair comprises two members, however, it may be possible to find additional compounds that may specifically bind to either member of a given specific binding pair.

The term "recovery tag" as used herein refers to a compound (or portion of a compound) that is a member of a specific binding pair of molecules. Recovery tags may also belong to a class of molecules that is not naturally-occurring. The recovery tag may belong to any class of macromolecule, e.g., polynucleotides, carbohydrates, polypeptides, and the like. Preferably, the recovery tag is an oligonucleotide. When the recovery tag is an oligonucleotide, the recovery tag may comprise none, part, or all of the template-annealing sequence of the recoverable primer.

When the recovery tag is an oligonucleotide, the recovery tag may optionally comprise a balancing polynucleotide sequence. The term "balancing polynucleotide" refers to polynucleotides that hybridize to the recovery tag binding compound, but do not specifically hybridize to the sequencing (or amplification) template. Balancing polynucleotides are optionally present on recoverable primers. The balancing polynucleotide may be used to equalize, i.e., balance, the melting temperatures of the duplex (or triplex) formed between the different recovery tag and the recovery tag binding compound pairs used together in the same reaction vessel. Similarly, the balancing polynucleotide may be used to equalize, i.e., balance, the melting temperatures of the duplex (or triplex) formed between the different recovery tag and the recovery tag binding compound pairs that are to be denatured under similar conditions.

The term "recovery tag binding compound" as used herein refers to the member of a specific binding pair that is not the recovery tag on a given recoverable primer. In embodiments of the invention employing polynucleotides as recovery tags, the recovery tag binding compound comprises a polynucleotide sequence that is complementary or partially complementary to the recovery tag polynucleotide of interest. Individual recovery tag binding compound molecules may comprise multiple copies of the complementary (or partially complementary) polynucleotide sequence. Branched polynucleotides, for example as described in published PCT patent application WO 96/016104 and published European patent application EP 646595, may be used to increase the effective concentration of binding sites for recovery tags.

The term "recoverable primer" refers to an oligonucleotide primer that comprises a recovery tag. Recoverable primers may be used to specifically prime a polynucleotide sequencing reaction, a polynucleotide amplification reaction, or other primer extension reaction, i.e., recoverable primers comprise a polynucleotide sequence that can specifically bind to a specific (usually pre-determined) site on a template for sequencing (or amplification). The portion of the recoverable primer that may site-specifically hybridize to a template is referred to herein as the "template-annealing sequence" of the recoverable primer. The template-annealing sequence is of sufficient length to specifically hybridize to a site or sites on the template of interest, typically 18–36 nucleotides in length. Template-annealing sequences for use in polynucleotide sequencing must hybridize to unique sites on the template of interest. The recovery tag is coupled to the primers in such a way as to avoid having the recovery tag interfere with the ability of the recoverable primer to site-specifically hybridize to the priming site, e.g., the recovery tag may be joined at, or proximal to, the 5' end of the recoverable primer. The particular means of coupling a recovery tag to an oligonucleotide primer depends upon the class of compound to which the recoverable tag belongs. When the recovery tag is a polynucleotide, the recovery tag is preferably coupled by polynucleotide linkage, e.g., a phosphate linkage. When the recovery tag is a protein, the recovery tag is preferably coupled by a bifunctional crosslinking agent such as DSS (disuccinimidyl suberate), SPDP (N-succinimidyl 3-(2 pyridyldithio propionate)), SATA (N-succinimidyl S-acetylthioacetate), and the like. Detailed protocols for methods of attaching labels to polynucleotides can be found in, among other places, G. T. Hermanson, *Bioconjugate Techniques,* Academic Press, San Diego, (1996).

When the recovery tag on a recoverable primer is a polynucleotide, the recovery tag may comprise all, part, or none of the template-annealing sequence of the recoverable primer. In some embodiments of the invention, the recovery tag may consist of some or all of the sequence of the recoverable primer. In other embodiments of the invention, the recovery tag does not comprise any portion of the template-annealing sequence of the recoverable primer. In still other embodiments of the invention, the recovery tag comprises a balancing polynucleotide. The entire recovery tag may be a balancing polynucleotide. Alternatively, the recovery tag may consist of a balancing polynucleotide and a portion of the template-annealing sequence adjacent to the balancing polynucleotide.

The recoverable primers for use either in polynucleotide sequencing or polynucleotide amplification embodiments of the invention (as well as other primer extension reactions) are capable of specifically hybridizing to target polynucleotide sequences under a given set of hybridization conditions. The criteria for designing sequence specific primers are well known to persons of ordinary skill in the art. Detailed descriptions of primer design criteria that provide for site-specific annealing can be found, among other places, in Dieffenbach and Dveksler, *PCR Primer, A Laboratory Manual*, Cold Spring Harbor, Cold Spring Harbor Press (1995), and Kwok et al, *Nuc. Ac. Res.* 18:999–1005 (1990). The template-annealing sequence portions of the primers are of sufficient length to permit site-specific annealing to template sites of interest. Primers for sequencing are designed to uniquely hybridize to a single template site. The template-annealing sequence of the recoverable primers may be either completely complementary or partially complementary to the bases of the target sequence, i.e., the annealing site. Preferably, the template-annealing sequence of the recoverable primers is completely complementary to the bases of the corresponding target sequence.

A sequencing ladder generated from a recoverable primer may be referred to as a "recoverable sequencing ladder." Additionally, the term "recoverable sequencing ladder" includes sequencing ladders that comprise the functional equivalent of recovery tags, such as sequencing ladders produced during non-recovery tag multiplex methods. A polynucleotide amplification product generated from a recoverable primer may be referred to as a "recoverable amplification product." Additionally, the term "recoverable amplification product" includes amplification products that comprise the functional equivalent of recovery tags, such as sequencing ladders produced during non-recovery tag multiplex methods.

The term "polynucleotide amplification reaction" as used herein refers to a broad range of techniques for the amplification of specific polynucleotide sequences. Examples of such amplification techniques include the polymerase chain reaction (PCR), ligase chain reaction, 3SR (Guatelli et al, *Proc. Natl. Aca. Sci. USA* 87:1874–1878 (1990), nucleic acid sequence-based amplification (NASB) (van Gemen et al., *J. Virol. Methods* 45:177–188 (1993). PCR is the preferred polynucleotide amplification reaction for purposes of the subject invention.

The Invention

The invention relates to methods and compositions for simultaneously generating a plurality of polynucleotide sequencing ladders, typically in a single reaction vessel, and analyzing the sequence information derived from the simultaneously generated sequencing ladders. The invention may be readily adapted for use with other primer extension reactions. Each sequencing ladder is formed from a recoverable primer having a unique recovery tag. Every polynucleotide member of a polynucleotide set that constitutes a sequencing ladder is labeled with essentially the same recovery tag (or a functional equivalent of a recovery tag). After the simultaneous generation of multiple sequencing ladders, the different polynucleotide sequencing ladders are separated from one another by binding the recovery tags (or functional equivalents of recovery tags) to recovery tag binding compounds that have been immobilized on solid supports. The recovery tag binding compounds are immobilized on the solid support in an addressable manner, i.e., the recovery tag binding compounds have distinct locations on the solid supports or are located on separate distinct identifiable solid supports. The binding of the polynucleotide sequencing ladders to the recovery tag binding compounds serves to separate the different polynucleotide sequencing ladders. The separated polynucleotide sequencing ladders may then be released from the solid support and subsequently resolved into the individual polynucleotide components of the sequencing ladders. The subject methods of separating sequencing ladders may be readily adapted to separate or capture a simultaneously generated plurality of polynucleotide amplification products or other simultaneously generated primer extension products. The methods of the invention are especially useful when used in conjunction with a fluorescence-based polynucleotide analysis apparatus, e.g., an automated sequencer.

The significance of the savings in the number of manipulations provided by the methods of the inventions becomes particularly important when high throughput sequence generation or high throughput nucleic acid amplification is required. Consider the following example in which 108 sequences are analyzed from each blood sample obtained from 96 subjects. Conventional methods involve the following steps: 96 template preparations, 10,368 PCR reactions (108×96), 10,368 DNA purifications, 31,104 (3×10368) transfers of purified DNA to sequencing reactions (assuming an average of three sequences to be generated from each PCR amplification), 31,104 purifications of sequencing reactions, and 31,104 loadings of sequencing gel lanes. The same amount of sequence information can be obtained by the methods of the invention as follows: 96 DNA preparations, 864 PCR reactions (nine 12-plex reactions for each sample), 27 hybridization reactions (96 samples at a time) to transfer and purify the PCR amplification products to 27, 96-well plates, 4 amplicons/well, 2,592 12-plex sequencing reactions, 312 selections of the sequencing reaction products (96 at a time) and loadings onto separation devices (96 at a time). Thus by using the subject methods of multiplexing sequencing and polynucleotide amplification, the number of manipulations may be reduced over thirty-fold.

The methods and compositions of the invention have numerous aspects that are advantageous when compared to earlier methods of polynucleotide sequencing. A significant advantageous aspect of the invention is that increased amounts of sequence information may be obtained from the same or similar amounts of reagents, thereby significantly lowering the costs associated with producing a given unit of sequence information. Another significant aspect of the invention is that multiple sequencing ladders may be formed simultaneously in the same reaction vessel. By simultaneously generating a plurality of sequencing ladders in the same reaction vessel, the number of sample handling manipulations is reduced. The invention also reduces the number or manipulations required for other primer extension reactions. Reducing the number of sample manipulations increases the speed with which sequence ladders can be generated and reduces the opportunities for sample handling errors. Other aspects of the invention that make it superior to conventional multiplex sequencing methods, e.g., the method of Church et al (U.S. Pat. No. 5,149,625), include the absence of a need for a membrane transfer (blotting) step and the absence of a need for subcloning the polynucleotides for sequencing into special vectors. Other advantages of the invention are that sequencing ladders, amplicons (polynucleotide amplification products), or other primer extension products may be purified, separated, or concentrated with a minimal amount of manipulations.

The degree of reduction in reagent consumption achieved by the methods of the invention is determined, in large part, by the degree of multiplexing. For example, a sequencing reaction that has been multiplexed two-fold, i.e., two sequencing ladders are generated simultaneously in a single reaction vessel, may reduce the requirement of some sequencing reagents up to two-fold. Similarly, a sequencing reaction that has been multiplexed eight-fold, i.e., eight sequencing ladders are generated simultaneously in a single reaction vessel, may reduce the requirements for some reagents up to eight-fold. Thus the invention exploits the "excess" polynucleotide synthetic potential in a single sequence ladder generation reaction. It was an unexpected result that large quantities (two-fold or more) of additional sequence information could be obtained using the similar quantities of DNA polymerase and other reagents that had been used to produce a single sequencing ladder in conventional sequencing procedures. In order to generate a sequencing ladder with an appropriate length range, relatively high levels of enzymes, dNTPs, chain terminators (labeled or non-labeled), etc., are required. Simply reducing the quantity of reagents used to generate a single polynucleotide ladder cannot be used to reduce reagent costs as dramatically as achieved with the subject methods because useful information from sequencing ladders will be lost. For example, reducing the concentration of the polymerase too much will reduce signal strength, thereby reducing read length. Another problem with simply reducing reagent concentration arises when the concentration of a reagent drops to near or below the Km of the DNA polymerase.

Although the foregoing discussion has been primarily concerned with multiplex methods of sequencing and polynucleotide amplification, it will be readily appreciated by those skilled in the art that the general principles of the inventions may readily be adapted to virtually any molecular biology technique involving the extension of primers. By using a plurality of recoverable primers, each having a unique recovery tag (or functional equivalent thereof), multiple primer extension reactions may be performed simultaneously and the reaction products subsequently separated on the basis of binding to immobilized recovery binding tag compounds. These numerous multiplexed methods of primer extension reactions used are considered to be embodiments of the subject invention. Chain termination sequencing (Sanger method) and PCR are examples of primer extension reactions. The methods of the invention may also be used to provide for multiplexed oligonucleotide ligation assays such as the type described in U.S. Pat. Nos. 4,883,750; 4,988,617; and 5,242,794.

The subject invention permits the multiplexing of sequencing reactions or amplification reactions, or other types of primer extension reactions, to varying degrees. The sequencing reactions may be multiplexed by a factor of two or more. Typically, multiplexing will be by a factor of between 2 and 20. However, the invention also includes embodiments in which multiplexing is by factors of greater than twenty.

The subject methods of multiplex sequencing involve the simultaneous generation of a plurality of polynucleotide sequencing ladders in the same solution. The method comprises the step of mixing a plurality of recoverable sequencing primers with one or more sequencing templates. The mixing may take place in a single reaction vessel. The act of mixing comprises placing the recoverable primers and the templates into the same solution, thereby permitting the primers to anneal at specific sites on the template (or templates) so that the primers may be extended. Optionally, the reaction vessels may be agitated to improve mixing of the solution components. The reaction vessel serves as a container for the primers, templates, enzymes, dNTPs, chain terminators, and other reagents required for sequence ladder generation. The reaction vessel may take on any of a variety of shapes and sizes that would be known to a person of ordinary skill in the art, such forms include, but are not limited to, Eppendorf tubes, sealed capillary tubes, covered multi-well plates, and the like. After or concurrent with the mixing step, the recoverable sequencing primers are subjected to conditions that permit the recoverable primers to hybridize (anneal) to their respective templates. The plurality of templates used in the subject methods may be present on the same or different polynucleotide molecules. For example, a single chromosome or plasmid may comprise a plurality of sequencing templates if the recoverable primers are selected so as to anneal to multiple regions of the same DNA molecule. Alternatively, individual recoverable primers may be designed to hybridize to a plurality of templates that are present as separate DNA molecules. Recoverable primers designed for sequencing may be used to prime both strands of the same polynucleotide sequence during the same sequence generating reaction. Examples of sequencing templates include chromosomal DNA, cDNA, RNA, or DNA inserted into cloning vectors, and the like. Optionally, the templates for sequencing may be polynucleotides generated by nucleotide amplification reactions such as PCR (polymerase chain reaction).

In embodiments of the invention in which the recoverable primers anneal to the same strand of the same template, the annealing sites on the templates may be sufficiently close to one another so that interactions between the two sites during sequencing ladder generation may be detected. For example, a first sequencing primer and second sequencing primer may be selected to anneal to the same chromosome such that the first primer anneals about 400 bases 5' with respect to the annealing site of the second primer. The intensity of the sequence ladder signal, i.e., the quantity of polynucleotide constituents of the sequencing ladder, produced from the first primer falls off abruptly (though not to undetectable levels) when the sequence ladders extends through the annealing site of the second primer. This decrease in intensity may be used to determine when the sequence information obtained from two primers is contiguous.

The subject methods of simultaneously generating a plurality of polynucleotide sequencing ladders comprise the step of forming sequencing ladders. Each of the sequencing ladders formed is derived from the recoverable primers added in the mixing step. Protocols for forming sequencing ladders are well known to persons of ordinary skill in the art. Chain termination sequencing is the preferred method of sequencing ladder generation for use in the subject methods. In a most preferred embodiment of the invention the sequencing ladders are formed by cycle-sequencing. A description of cycle sequencing can be found, among other places, in Murray V., *Nucl. Acid. Res.*, 17:8889 (1989). Typically, cycle-sequencing is a sequencing ladder generating technique comprising the following steps: (a) the hybridization of a primer oligonucleotide to a template for sequencing so as to form a primed template, (b) extending the primer with a DNA polymerase, (c) ending the extension reaction with a chain terminator (e.g., a dideoxynucleotide terminator), (d) denaturing the primed template, (e) repeating steps (a) to (d) for multiple cycles. Increasing the number of cycles may be used to increase the amount of labeled polynucleotide produced, thereby compensating for relatively small amounts of starting material.

Many different methods of chain terminator sequencing may be used to obtain the sequence information from a given template. The different methods may involve variations in parameters such as the site of labeling (on the primer or on the chain terminator); the identity of the labels employed, the number of different labels employed, and the like.

In one embodiment of the invention, e.g., labeled terminator sequencing, sequence information may be obtained from a given template and a single recoverable primer by using four chain terminators, each chain terminator corresponding to a different nucleotide base and labeled with a distinctive fluorescent label.

In another embodiment of the invention, e.g., labeled primer sequencing, the recoverable primers are labeled and four distinct recoverable primers, each annealing to the same template site, but having a distinctive fluorescent label, are used in four separate reaction vessels to obtain the sequence of each template in the multiplexed sequencing reaction. For example, a first set of four labelled recoverable primers are prepared to prime at the same location on a given template. Each of these primers in the set is tagged with a different detectable label (four spectrally distinct labels are used). The recovery tag on each of the primers in a set is labeled with the same or different recovery tags (preferably the same recovery tag is used for each member of the set). Additional four primer sets are prepared for each template to be sequenced. The different members of each set of primers are then distributed between four reaction vessels, such that each vessel contains multiple primers (and templates) but only one primer from each primer set. A chain termination sequence ladder generating reaction is then prepared in each vessel, using a single type of chain terminating dideoxynucleotide in each vessel (A, G, C, or T). After the sequencing reactions are completed, a solid support, e.g., a macroscopic bead (or beads) having immobilized recovery tag binding compounds specific for the recovery tags present on all of the recoverable primers of a given set of primers is sequentially transferred between the solutions in each vessel; alternatively the reaction vessel contents of the different vessels may be mixed together prior to contacting the macroscopic bead. The process of contacting reaction vessel contents is repeated using different immobilized recovery tag binding compounds so as to provide for the isolation of each sequencing ladder set.

In order to generate sequencing ladders amenable to separation and analysis on automated instrumentation for the separation and detection of fluorescently labeled polynucleotides, such as the ABI 377 or ABI 310 (available from Perkin-Elmer, Applied Biosystems Division, Foster City, Calif.) the polynucleotide sequencing ladders generated may be fluorescently labeled. Descriptions of automated sequencing apparatus can be found, among other places, in U.S. Pat. Nos. 4,232,769; 4,603,114; 4,704,256; 4,811,218; 5,277,780; 5,290,419; 5,307,148; 5,366,608; 5,384,024; and 5,543,026. The fluorescent label may be attached to the recoverable primer or to the chain terminator. Suitable fluorescent labels include, but are not limited to 6-carboxyfluorescein (6-FAM), 5-carboxyfluorescein (5-FAM), 6-carboxy-4,7,2',7'-tetrachlorofluorescein (TET), 6-carboxy-4,7,2',4',5',7'-hexachlorofluorescein (HEX), 5-(and 6)carboxy-4',5'-dichloro-2'7'-dimethoxyfluorescein (JOE), and 5-carboxy-2',4',5',7'-tetrachlorofluorescein (ZOE), tetramethylrhodamine (TAMRA), 4,7-diclorotetramethyl rhodamine (DTAMRA), rhodamine X (ROX), rhodamine 6G (R6G), rhodamine 110 (R110), and the like. Descriptions of suitable fluorescent labels can be found, among other places, in U.S. Pat. No. 5,366,860 (Bergot), U.S. Pat. No. 5,188,934 (Menchen), U.S. patent application Ser. No. 08/626,085 (filed Apr. 1, 1996), Lee et al, 20(10):2471–2483 (1992). As described in Mathies PCT patent publication WO 95/21266, multiple fluorescent labels may be used in conjunction with one another so as provide for resonance energy transfer between fluorescent labels in order to obtain the desired spectral characteristics. Particularly preferred for use as dyes are the dye molecules described in U.S. patent application Ser. No. 08/642,330 filed May 3, 1996 and Ser. No. 08/726,462 Oct. 4, 1996. In other embodiments of the invention, non-fluorescent labels, such as enzymatic labels, radioactive labels, chemiluminescent labels, and the like, may be used to label sequencing primers or the chain terminators.

Numerous protocols for chain termination sequencing of polynucleotides have been published and are well known to persons skilled in the art of molecular biology. These published techniques may be used in conjunction with the subject methods for simultaneously generating a plurality of polynucleotide sequencing ladders (and separating the ladders generated) so as to realize significant savings with respect to costly reagents such as thermostable enzymes, fluorescently labeled primers, and fluorescently labeled terminators. Conventional polynucleotide sequencing techniques usually employ at least 8 to 12 units of Taq DNA polymerase for each sequence ladder generated. The term "unit" as used herein with respect to the thermostable polymerase sold under the name AmpliTaq DNA polymerase (Perkin Elmer, Applied Biosystems Division, Foster City, Calif.) is defined as the amount of enzyme that will incorporate 10 nmol dNTP's into acid insoluble polynucleotide material in 30 minutes at 74° C.; this definition may be used to determine corresponding amounts of other thermostable DNA polymerases. It will be appreciated by those skilled in the art that the foregoing definition of "unit" may be applied to many DNA polymerases and is not limited to AmpliTaq DNA polymerase. Thus, by employing the methods of the invention, sequencing ladders may be produced by using approximately 4 to 6 units (for two-fold multiplexing), or less, of DNA polymerase for each sequencing ladder generated. It will also be appreciated by those skilled in the art that a variety of different DNA polymerases, both thermostable and heat-labile, may be used for sequence ladder generation and that similar degrees of reductions in reagent usage can be achieved with different DNA polymerases. Numerous different DNA polymerases or mixtures of DNA polymerases may be used for sequence ladder generation. When the sequence ladders are generated through cycle sequencing, the DNA polymerase used is preferably a thermostable DNA polymerase. Examples of suitable thermostable DNA polymerases include Taq™ (Perkin-Elmer, Norwalk Conn.), Vent™ (New England Biolabs, Beverly Mass.), Deep Vent™ (New England Biolabs, Beverly Mass.), *Pyrococcus furiosus* DNA polymerase (Stratagene, La Jolla Calif.), *Thermotoga maritima* DNA polymerase, and AmpliTaq DNA polymerase, FS™ polymerase, and Ampli DNA polymerase, Taq FS DNA polymerase. Taq™ FS DNA polymerase (Perkin-Elmer, Norwalk Conn.) is particularly preferred for use in cycle sequencing.

After a sufficient amount of polynucleotide is formed, i.e., an amount readily detectable by the selected analytical instrument, the recovery tags on the sequencing ladders (or amplification products) are permitted to bind to recovery tag binding compounds that have been immobilized on a solid support in a spatially addressable manner. For the sake of convenience this step may be referred to as a "pull-out" or "pulling out." By binding the recovery tags to their cognate immobilized recovery tag binding compounds, the sequencing ladders (or amplification products) are separated from one another and purified through immobilization on a solid support. Recovery tags (and their respective recovery tag binding compounds) are selected so as to avoid the binding of the recovery tags at improper locations, e.g., different recovery tags oligonucleotides are preferably non-cross hybridizing. Binding between the recovery tags and their cognate recovery tag binding compounds may be achieved by contacting immobilized recovery tag binding compounds with the solution (or solutions) in which sequence ladder generation (or nucleic acid amplification) has occurred. Binding between the recovery tags and their cognate recovery tag binding compounds does not require the binding of 100% (or even a substantial portion) of the labeled polynucleotides in order to be effective for purposes of the invention. The quantity of polynucleotide bound need only be sufficient to produce a detectable signal from the label on the polynucleotides released in subsequent steps. Contact between the recovery tag binding compounds and the recovery tags on the sequencing ladders may be initiated either after sequencing ladder formation has been completed or concurrent with the generation of sequencing ladders (or generation of amplification products or other primer extension reaction products). Preferably, contact is initiated after sequencing ladder generation (or nucleic acid amplification) is completed. Solutions containing the recoverable sequencing ladder polynucleotides (or nucleic acid amplification products) may be modified by the addition of reagents in order to enhance the binding between the recovery tags and the recovery tag binding compounds (e.g., so as to alter the pH, ionic strength, or salt concentration of the solution). The binding between the recovery tags and the recovery tag binding compounds may also be modified by the addition of DNA binding proteins or other DNA binding compounds. Contact between the immobilized recovery tag binding compounds and the recovery tags should be for a period of time sufficient to permit the binding of a detectable amount of polynucleotide to the immobilized recovery tag binding compounds. The amount of time required to permit sufficient binding of the recovery tags will vary in accordance with the specific recovery tag and recovery tag binding compounds selected for use in a given embodiment. The amount of time required to permit sufficient binding of the recovery tags may also vary in accordance with the effective concentrations of specific recovery tag and recovery tag binding compounds. Similarly, the conditions required to permit binding of the recovery tags will vary in accordance with the specific recovery tag and recovery tag binding compounds selected for use in a given embodiment. When the recovery tags and recovery tag binding compounds are both polynucleotides, well-established empirically-derived formulae and other information concerning nucleic acid duplex (or triple helix) formation may be used to optimize the conditions and time for binding between the recovery tags and the recovery tag binding compounds. The kinetics of nucleic acid hybridization and denaturation are well understood and may be used to calculate the time and conditions required for binding and release. Information on nucleic acid hybridization kinetics may be found in, among other places, Berger and Kimmel, *Guide to Molecular Cloning Techniques,* Academic Press, San Diego, (1987), Cantor and Schimmel, *Biophysical Chemistry, Part III: The Behavior of Biological Macromolecules,* W. H. Freeman, NY, (1980), Saenger, *Principles of Nucleic Acid Structure,* Springer-Verlag, N.Y. (1989), and the like.

The step of binding recovery tags to their cognate recovery tag binding compounds may be sequential or simultaneous. In sequential binding, for example, a mixture containing multiple recovery tags is contacted with a first immobilized recovery tag binding compound and subsequently contacted with a second immobilized recovery tag binding compound. The recovery tag containing mixture may be repeatedly contacted with additional immobilized recovery tag binding compounds. In simultaneous binding, a mixture containing multiple recovery tags is contacted with a set of immobilized recovery tag binding compounds comprising more than one different immobilized recovery tag binding compound. Sequential and simultaneous binding procedures may be combined by performing sequential binding with sets of immobilized recovery tag binding compounds comprising more than one recovery tag binding compound.

A releasing step is performed in order to provide for the analysis of the polynucleotide sequencing ladders (or amplification products) that have been bound to the immobilized recovery tag binding compounds. The releasing step serves to release the polynucleotide sequencing ladders (or amplification products) that have been bound to the solid support by means of their specific binding to their cognate recovery tag binding compounds. Typically the sequencing ladders (or amplification products are released by disassociating the recovery tag binding compounds from the recovery tags; however, release may also be effected by severing the connection (either covalent or non-covalent) between the recovery tag binding compound and the solid support. Importantly, the releasing step is performed in such a manner so as to maintain the separation of the different sequencing ladders that was introduced during the binding of the recovery tags to the immobilized recovery tag binding compounds. In order to permit the releasing step to maintain the separation of the sequencing ladders, the separated released sequencing ladder polynucleotides (or amplification products) are individually collected concurrent with the releasing process. Collecting of the released polynucleotide sequencing ladders (or amplification products or other primer extension products) may be achieved by numerous different techniques and configurations of the devices used to collect the released polynucleotides. The range of suitable collection techniques is dependent, in part, upon the particular configuration of the solid support used for immobilization of the recovery tag binding compounds. Preferably, the collection of the released polynucleotide sequencing ladders (or amplification products or other primer extension products) is directly integrated with the loading of the released polynucleotide sequencing ladders into a polynucleotide separation device, e.g., an electrophoresis gel. For example, release of the recoverable sequencing ladders may take place in the loading regions of a sequencing slab gel or capillaries, wherein a different sequencing ladder is deposited into each separate loading region. In other embodiments of the invention, the released sequencing ladders are collected separately in individual collection vessels, such as tubes or microtiter dish wells, and temporarily stored prior to loading onto a polynucleotide separation device. For example, macroscopic beads having recovery tag binding compounds immobilized on their surfaces may be transferred to Eppendorf tubes after binding to recoverable sequencing ladders so as to provide for the release of the sequencing ladders in the Eppendorf tubes.

The released sequencing ladders may then be transferred to an electrophoretic separation device for analysis.

The specific means selected for releasing the recovery tags from the solid support will vary in accordance with the specific recovery tags and recovery tag binding compounds selected for a given embodiment of the invention. The releasing step does not require the release of 100% of the bound sequencing ladders (or amplification products) in order to be effective. The quantity of polynucleotide released need only be sufficient to produce a detectable signal from the label on the released polynucleotides. Release may be achieved by any of a variety of means adapted to the specific recovery tags and recovery tag binding compounds employed in the specific embodiments. Different recovery tags may be released by the same or different releasing procedures in given embodiments of the invention. Preferably, all recovery tags in a given embodiment of the invention are released by the same procedure. When the recovery tags and recovery tag binding compounds are both polynucleotides, release is preferably achieved by denaturation of the duplex (or possibly triple helix) formed between the recovery tags and their corresponding recovery tag binding compounds. Factors influencing the denaturation temperature of multi-stranded polynucleotides, e.g., cation concentration, are well known to persons of ordinary skill in the art of molecular biology. Accordingly, release of the polynucleotide recovery tags may be achieved by subjecting the bound polynucleotides to elevated temperatures or the addition of denaturing agents such as urea or formamide in appropriate concentrations. Additionally, polynucleotide recovery tags may be released by enzymatic means. For example, by providing specific nucleotide recognition sequences in double-stranded form, restriction endonucleases may be used to effect release. Type IIS restriction endonucleases are particularly suitable for this task because the recognition sequence of a type IIS restriction endonuclease is separate from the cleavage site, thereby permitting the recognition sequence to be located within polynucleotides serving as recovery tag binding compounds. Other nucleases specific for the double-stranded region of recovery tag-recovery tag binding compound interaction may be used to effect release of bound sequencing ladders or amplicons from recovery tag binding compounds. A combination of nuclease resistant nucleotides (or nucleotide analogs) in the sequencing ladders and nuclease sensitive nucleotides (or nucleotide analogs) in the recovery tag and/or recovery tag binding compounds may be used to increase the range of nucleases suitable for release. In another embodiment of the invention, release of the sequencing ladder polynucleotides may be achieved by conventional chemical reactions rather than enzymatically catalyzed chemical reactions. For example, a ribonucleotide (as opposed to a deoxyribnucleotide) may be incorporated into the recovery tags and recovery tag binding compounds so as to provide for cleavage (and hence release) though exposure to an alkaline environment. When antibodies are used as recovery tag binding compounds, release may be effected through high salt concentrations, elevated temperature, or pH adjustments. In other embodiments, the recovery tags may be released from the solid support by breaking the linkage (typically covalent) between the recovery tag binding compound and the solid support.

In a preferred embodiment of the invention, the recovery tags and recovery tag binding compounds are polynucleotides. The release of polynucleotide recovery tags is preferably achieved through denaturation. The use of sets of recovery tags that can be simultaneously released under similar denaturation conditions greatly simplifies the instrumentation required for the releasing step because it is unnecessary to provide separate denaturation environments for each of the bound recovery tags. Sets of recoverable primers that have recovery tags capable of being released under the same or similar denaturation or releasing conditions are referred to herein as "integrated" sets of recoverable primers. In order to provide an integrated set of primers, the recovery tags on the primers are selected so as to have Tm's that are within 15° C. of each other, preferably, within 10° C., and more preferably within 5° C. of each other. The Tm is the denaturation temperature as measured between the immobilized recovery tag binding compound and the recovery tag. The Tm may be determined either empirically or by reference to empirically determined formulae for Tm calculation. Examples of such formulae can be found among other places in Berger and Kimmel, *Guide to Molecular Cloning Techniques,* Academic Press, San Diego, (1987), Cantor and Schimmel, *Biophysical Chemistry, Part III: The Behavior of Biological Macromolecules,* W. H. Freeman, NY, (1980), Saenger, *Principles of Nucleic Acid Structure,* Springer-Verlag, N.Y. (1989), and the like. The use of integrated sets of recoverable primers is particularly useful for kits for multiplex sequencing or multiplex amplification assays. For example, integrated sets of recoverable primers may be used to simultaneously sequence several loci correlated with genetic diseases. Similarly, integrated sets of recoverable primers may be used in conjunction with the subject methods of separating a plurality of polynucleotide amplification products produced from recoverable primers.

In order to provide for the binding of recovery tags to recovery tag binding compounds, the subject methods may employ solid supports comprising one or more immobilized recovery tag binding compounds; such solid supports are referred to herein as polynucleotide recovery devices. The term "solid support" as used herein includes both single structures and collections of individual components such as a collection of beads or fibers. The solid supports for use in the subject methods and devices may be formed from a variety of materials, including but not limited to, metals, polymers (e.g., as polyethylene, polypropylene, polystyrene, polyacrylamide, and the like), glasses, or polysaccharides (e.g., agarose, cellulose). Solid supports may be formed from a material or materials selected to be compatible with the immobilization of the recovery tag binding compounds. The recovery tag binding compounds are immobilized on the solid support in an addressable manner. The term "addressable" is used to indicate that the location of the recovery tags on the support is predetermined such that the desired recovery tag can be found by selecting a specific location, i.e., an "address", on the solid support (or by selecting a specific solid support unit). The term "addressable" as used herein with reference to solid supports, includes the beads and other similar solid support units comprising a recovery tag binding compound or compounds uniformly distributed over the support. Each recovery tag binding compound has a unique location on the solid support (or is attached to a unique solid support). The different recovery tag binding compounds are separated from one another on the solid support in those embodiments of the invention having a plurality of recovery tag binding compounds immobilized on the same solid support. Preferably, the different recovery tag binding compounds are separated from one another by regions of solid support that lack recovery tag binding compounds. In one embodiment of the invention, a multiple projection electrophoresis loading device such as a well-loading gel comb may be used as a solid support. Suitable multiple projection electrophoresis loading devices have multiple projections, each projection with a different recovery tag immobilized on the projection. In other embodiments of the invention, the solid support may take the form of a planar "chip" comprising distinct spatially addressable recovery tag binding compounds. Techniques for synthesizing oligonucleotides at predetermined locations on chips may be found in U.S. Pat. Nos. 5,527,681; 5,424,186; 5,143,854; 5,405,783; 5,445,934; and 5,510,270. In another embodiment of the invention, a collection of several beads, preferably porous macroscopic beads, are used as a solid support, wherein each of the beads comprises a unique immobilized recovery tag binding compound. The macroscopic beads, and hence the recovery tag binding compounds, may be distinguished from one another by providing some identifying label on each bead (or collection of similar beads) such as color-coding, symbols, transponder labeling, shape, size, magnetic labeling, density, and the like. Alternatively, the beads may be distinguished from one another based upon the polynucleotide sequence information obtained from the sequencing ladders immobilized on the beads (or from the size of the amplification products). The beads may be of any of a variety of shapes, including spherical, cubic, pyrimidal, planar, or irregular. Preferably, the beads are of shapes and sizes that facilitate the packing of numerous beads in a small volume so as to maximize contact between the recovery tag containing solution and the beads. In addition to macroscopic beads, differentially labeled microscopic beads may also be used. The distinction between microscopic beads and macroscopic beads is indicative of the methods by which the beads may be physically manipulated. Generally, macroscopic beads are of a size that readily permits the manipulation of individual beads, whereas microscopic beads are too small to permit the convenient manipulation of individual beads, but may be manipulated in groups by techniques such as magnetic transfer or centrifugation. Generally, macroscopic beads have an approximate mean diameter (largest dimension) of between about 0.5 mm to 5 mm, the range of 1 mm to 3 mm being preferred. Microscopic beads are generally smaller than 0.5 mm in mean diameter.

The recovery tags of the sequencing ladders (or amplification products, i.e., amplicons) may be separated from one another by sequentially (or in parallel) binding the recovery tags on a plurality of sequencing ladders (or amplification products) to different recovery tag binding compounds immobilized on different solid supports, such as beads. For example, a composition comprising four sequencing ladders, each ladder having a unique recovery tag, may be incubated with a plurality of macroscopic beads (magnetic or otherwise), wherein each bead comprises an immobilized recovery tag binding compound specific for a recovery tag on one of the sequencing ladders. The beads, having bound to recovery tags, are subsequently removed. The removed beads may then be washed so as to remove non-specifically bound polynucleotides. The process is then repeated for second, third, and fourth recovery tag binding compounds immobilized on different beads and introduced into the same sequencing ladder containing compositions as the first bead. After the washing process has been completed, the recovery tags may be released. In another example of sequential recovery, beads comprising immobilized recovery tag binding compounds are contacted with a first solution comprising recoverable sequencing ladders (or amplification products), removed from the solution, washed, and contacted with a second solution comprising recoverable sequencing ladders (or amplification products) removed from the solution. Such steps may be repeated several times until the recovery tags are released from the beads.

In the polynucleotide recovery devices of the invention, the recovery tag binding compounds are attached to the solid support in a manner so as to permit the recovery tag binding compounds to interact with their respective recovery binding tags. A variety of techniques may be used to immobilize the recovery tag binding compounds on the solid support. The specific techniques selected will depend upon the choice of recovery tag binding compounds and solid support materials. Techniques for immobilizing proteins and polynucleotides are well known to persons of ordinary skill in the art of molecular biology. For example, proteins may be conjugated to solid supports through formaldehyde, DMS (dimethyl suberimidate), and reductive amination. Polynucleotides may be conjugated to solid supports through agents such as 1,3-diaminopropane, 3,3'-iminobisproplyamine, EDC (1-ethyl-3-(3-dimethylaminopropyl)carbodiimide hydrochloride), SPDP (N-succinimidyl 3-(2 pyridyldithio propionate)), and SATA (N-succinimidyl S-acetylthioacetate). Examples of moieties for linking oligonucleotides to solid supports can be found in Pon et al, *Biotechniques*, 6:768–775 (1988); Webb, U.S. Pat. No. 4,659,774; Barany et al, PCT patent application PCT/US91/06103; Brown et al, *J. Chem. Soc. Commun.*, 1989:891–893; Dahma et al, *Nucleic Acids Res.* 18:3813–3821 (1990); Beattie et al, *Clinical Chemistry*, 39:719–722 (1993); Maskos and Southern, *Nucleic Acids Res.*, 20: 1679–1684 (1992). The recovery tag binding compounds may be attached to the support through either direct or indirect linkages. The term "direct linkage" refers to the covalent binding of the recovery tag binding compound to the solid support, including covalent bonding through a linker (and optionally a spacer arm). The term "indirect linkage" refers the binding of the of the recovery tag binding compound to the solid support through a specific binding pair, e.g., biotin-avidin (or streptavidin) pairs or antigen-hapten, wherein one member of the pair is joined to the recovery tag binding compound and the other member of the pair is joined to the solid support.

In addition to providing methods for simultaneously generating a plurality of sequencing ladders and subsequently separating the ladders, the invention also provides methods for separating a plurality of simultaneously generated polynucleotide amplification products. The subject polynucleotide amplification product separation methods may be performed by modifying the subject multiplex sequencing ladder generation and separation methods so as to generate recoverable polynucleotide amplification products rather than recoverable sequencing ladders. Methods for polynucleotide amplification are well known to persons of ordinary skill in the art. Detailed protocols for polynucleotide amplification can be found in, among other places, Dieffenbach and Dveksler, *PCR Primer, A Laboratory Manual,* Coldspring Harbor Press, Coldspring Harbor, N.Y. (1995), McPherson et. al, *PCR A Practical Approach. Vol* 1, IRL Press Oxford, England (1991), McPherson et. al, *PCR A Practical Approach. Vol* 2, IRL Press Oxford, England (1995), U.S. Pat. No. 4,683,202, U.S. Pat. No. 483,195, and U.S. Pat. No. 4,965,188. Furthermore, detailed protocols for multiplex PCR can be found in, among other places, Shuber et al, Genome Research, 5:488–493 (1995), Eggerding, *PCR Methods and Applications,* 4:337–345 (1995), Cuppens et al, *Molecular and Cellular Probes,* 6:33–39 (1992), and U.S. Pat. No. 5,582,489. The subject methods of separating a plurality of simultaneously generated polynucleotide amplification products involve performing polynucleotide amplification reactions, wherein at least one member of a pair of amplification primers is a recoverable amplification primer. When both members of a pair of amplification primers are recoverable primers, the amplification products produced will have two recovery tags. When both members of a pair of amplification primers are recoverable primers, the recovery tags may be the same or different from one another. The invention also includes embodiments in which recovery tags and recovery tag binding compounds may be selected so as to provide for the isolation of selected sets of nucleic acid amplification fragments rather than the isolation of individual amplification fragments. Generally, the subject methods of separating a plurality of simultaneously generated polynucleotide amplification products (through multiplex PCR or similar amplification techniques) include the steps of mixing a plurality of recoverable amplification primers having recovery tags with a plurality of amplification templates. After the mixing step, the amplification templates are amplified using at least one recoverable primer so as to form a plurality of amplification products, each product having a recovery tag, wherein the amplification reaction is in a single reaction vessel. Next, the recovery tags, and hence the amplification products, are permitted to bind to recovery tag binding compounds that have been immobilized on a solid support in a spatially addressable manner. Subsequently, the bound amplification products are released from the solid supports.

The invention also provides for recoverable primers having oligonucleotide recovery tags that cannot be replicated during a nucleic acid amplification reaction. Thus, when such primers are employed in polynucleotide amplification reactions, an extension product complementary to the recovery tag oligonucleotide is not generated. These recoverable primers are referred to herein as "hinged primers." Hinged primers are particularly useful in multiplex polynucleotide amplifications as described herein because there is no need to denature (or prevent from renaturing) a double-stranded polynucleotide comprising the recovery tag so that the recovery tag oligonucleotide may bind to a recovery tag binding compound that is a complementary oligonucleotide. Recoverable primers that comprise a recovery tag that can be replicated during nucleic acid amplification generate a polynucleotide sequence complementary to the recovery tag sequence during the process of polynucleotide amplification. This complementary sequence can significantly compete with the binding of a recovery tag to an immobilized recovery tag binding compound (e.g., an immobilized complementary oligonucleotide). Accordingly, hinged primers may be advantageously employed in many of the methods of the invention where it is desirable to efficiently recover the amplification products through binding to compounds that are immobilized on solid supports.

Hinged primers are recoverable primers that have oligonucleotide recovery tags that cannot be replicated by a DNA polymerase during a nucleic acid amplification reaction. There are many different oligonucleotides that may be used as recovery tags that cannot be replicated during a nucleic acid amplification reaction. In one embodiment of hinged primers, the recovery tag is an oligonucleotide analog that is not capable of being replicated by the DNA polymerase used in the amplification reaction. Examples of such non-replicable oligonucleotide analogs include, but are not limited to peptide-nucleic acids (PNAs) and the like. PNAs synthesis and structure is described in, among other places, Egholm et al, *J. Am. Chim Soc.* 114:1895–1897 (1992), Kosynkina et al, *Tet. Lett.* 35:5173–5176, Dueholm et al, *J. Org. Chem.* 59:5767–5773 (1994). In another embodiment of hinged primers, the recovery tag may be an oligonucleotide that could otherwise be replicated by a DNA polymerase, but is blocked by a non-replicable linker joining the recovery tag to template-annealing sequence portion of the recoverable primer. Such non-replicable linker may be oligonucleotide analogs. Alternatively, in some embodiments of the invention the non-replicable linkers may have little or no structural similarity to naturally occurring polynucleotides. Examples of non-replicable linkers that are oligonucleotide analogs include poly-5'→3'-deoxyribose (i.e., DNA without nucleoside bases), peptide nucleic acids and the like. Examples of non-replicable linkers that are not oligonucleotide analogs include polyethylene glycol hydrocarbons, and the like. Methods of conjugating linkers to polynucleotides are well know to those of ordinary skill in the art, examples of such conjugation techniques can be found in Hermanson, *Bioconjugate Techniques,* supra. Typically, the non-replicable linker is located at the 5' end of the template-annealing region of the hinged primer, thereby minimizing interference with the activity of the DNA polymerase catalyzing the extension reaction. IN alternative embodiments of the invention, the recovery tag of a hinged primer may be rendered non-replicable in an amplification reaction by virtue of the site of attachment (or orientation) of the recovery tag to the primer, e.g., at a position other than the 5' end primer.

The invention also provides methods of polynucleotide amplification using hinged primers. These amplification methods may be multiplexed so as to take full advantage of the properties of hinged primers. The subject methods include the step of mixing at least one hinged primer with one or more polynucleotide template for amplification under polynucleotide amplification conditions. In general, hinged primers may used in the same way as other recoverable primers in multiplexed polynucleotide amplification reactions of the invention.

Although the foregoing description of the invention has been primarily concerned with the use of recoverable primers for multiplexed polynucleotide amplification, it will be appreciated by those skilled in the art that the methods may be readily adapted for use without recoverable primers. Oligonucleotide primers without recovery tags may be used to generate recoverable sequencing ladders or recoverable polynucleotide amplification products; these methods are referred to as "non-recovery tag multiplex methods." Non-recovery tag multiplex methods employ the functional equivalents of recovery tags. In non-recovery tag based multiplex method embodiments of the methods of the invention, primers without recovery tags may be substituted for recoverable primers by using recovery tag binding compounds that are polynucleotides comprising a polynucleotide sequence capable of specifically hybridizing to a polynucleotide sequence that is newly formed during either sequencing ladder generation or the process of polynucleotide generation (see FIGS. 1D and 1E). These newly generated polynucleotide sequences are the portions of the polynucleotide ladder or amplicon other than the primer sequence. Suitable recovery tag binding compounds for use with such primers may specifically bind to either newly synthesized polynucleotide or to a combination of newly synthesized polynucleotide and primer polynucleotide that is immediately adjacent to the 3' end of the primer. The recovery tag binding compounds may be designed to bind to newly generated polynucleotide sequences that are on the polynucleotide strand complementary to the polynucleotide strand comprising the primer. For example, a recovery tag binding compound may be a polynucleotide complementary to the polynucleotide sequence in an amplicon that forms a duplex with one of the amplification primers. In order to design recovery tag binding compounds for use in the aforementioned embodiments of the invention, sequence information about a portion of the newly generated sequence must either be known or conjectured. Non-recovery tag based multiplex methods are of particular interest because they permit primers with "universal" template-annealing sequences to be used in the multiplexed sequencing and nucleic acid amplification methods of the invention. The term "universal" is used to indicate that a given template-annealing region of a primer may used with a wide range of templates because the region of the template that the primer anneals to is common to multiple templates.

Figure 4:
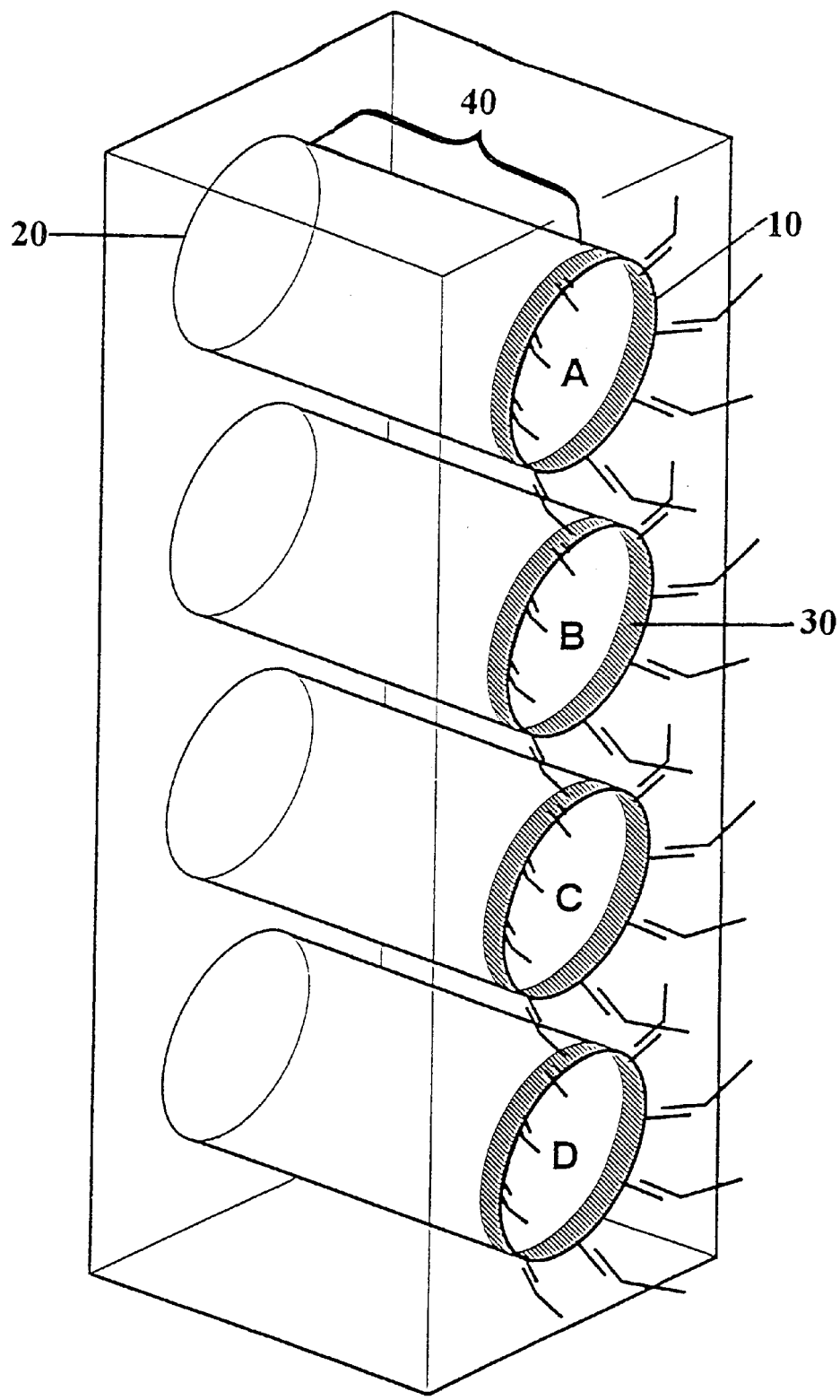
FIG. 4. This figure is a diagram of a microchannel device for the separation of polynucleotides. The input ports 10 and output ports 20 are indicated. The region of recovery tag binding compounds 30 that are immobilized near the input ports are also indicated. The channels 40 are indicated. Schematic representations of recovery tag binding compounds are indicated by straight lines joined at 30. Recoverable polynucleotides are indicated by the bent lines near the recovery tag binding compounds.

The invention also provides polynucleotide recovery devices. The subject devices are designed so as to facilitate the methods of the invention by providing for the binding of the recovery tags (or functional equivalents of recovery tags) to the recovery tag binding compounds. The polynucleotide recovery devices of the invention comprise a plurality of recovery tag binding compounds, wherein each of the recovery tag binding compounds is immobilized to the solid support in an addressable manner. Different recovery tags present on the same device are separated from one another, preferably separated by the solid support medium. Generally, the different recovery tag binding compounds are present in equal amounts; however, amounts of the different recovery tag binding compounds may be normalized so as to account for differences in binding affinity between different specific binding pairs. The recovery tag binding compounds may be uniformly separated from each other in a regular array. In another embodiment of the invention, the solid support is an array of capillary channels (FIG. 4). The capillary channels are positioned parallel to one another. The capillary channels may be in the form of capillary tubes or may be channels in a block, rather than individual capillary tubes. Preferably, the capillary channels are identical to each other in all dimensions. The diameter of the capillary channels is typically, although not necessarily in the range of 25 to 75 $\mu$m. Capillary channels with comparable cross-sectional areas may be used. Preferably, the channels are of uniform diameter along their length. Each capillary channel has an input port 10 and an output port 20. Each capillary channel forms a continuous path for electrophoretic separation. The input ports are for the introduction of polynucleotides for separation. The output ports serve to provide for the removal of the separated polynucleotides and to provide a current path for electrophoresis. The subject polynucleotide recovery devices comprise a plurality of recovery tag binding compounds, wherein each of the recovery tag binding compounds is immobilized proximal to the input ports of the capillary channels. The recovery tag binding compounds may be immobilized within the input port or immobilized adjacent to the input port. Each input port has a different recovery tag binding compound. Preferably, the recovery tag binding compounds are polynucleotides.

Figure 3:
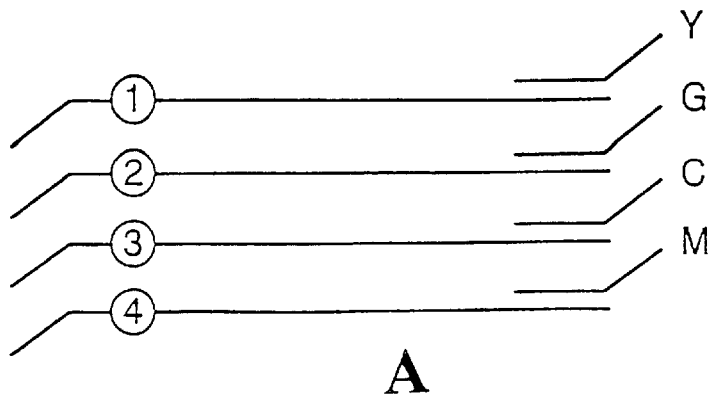
FIG. 3. This figure is a schematic representation of an embodiment of the invention for 4-fold multiplex polynucleotide sequencing. In 3A, the DNA sequence generating reactions occur simultaneously in the same tube, whereby recoverable sequencing ladders are produced. The recoverable primers have a balancing sequence and the recovery tag binding compounds hybridize to the balancing sequence. The four templates are indicated by the numbers 1–4. The different recoverable primers, each with a different recovery tag are indicated by the letters C, G, Y and M. 3B shows four different sequencing ladder generations taking place in the same tube. 3C shows separated sequencing ladders annealed to different projections of a well-loading gel comb. The recovery tag binding compounds are immobilized to different teeth (projections) of the comb.
Figure 3:
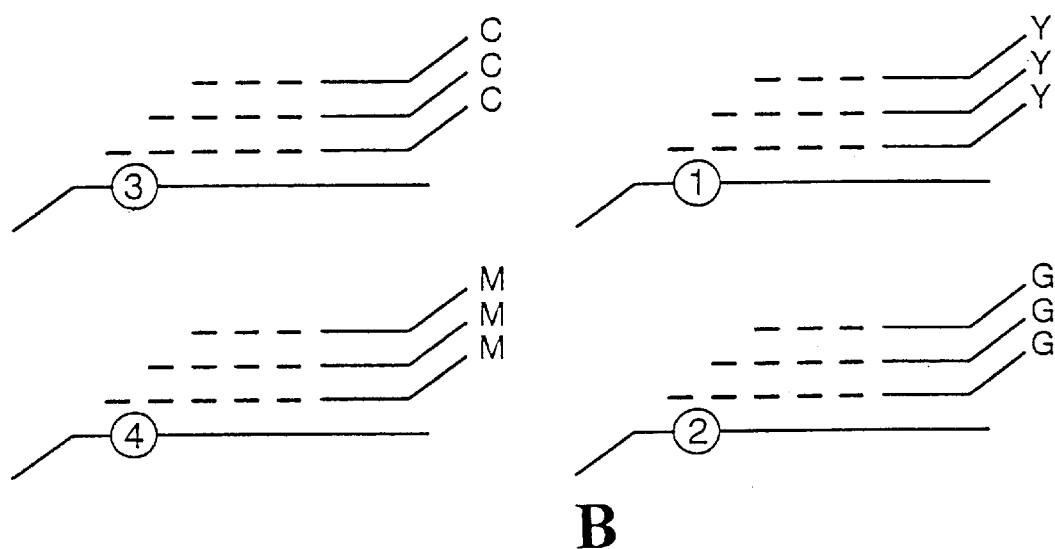
Figure 3:
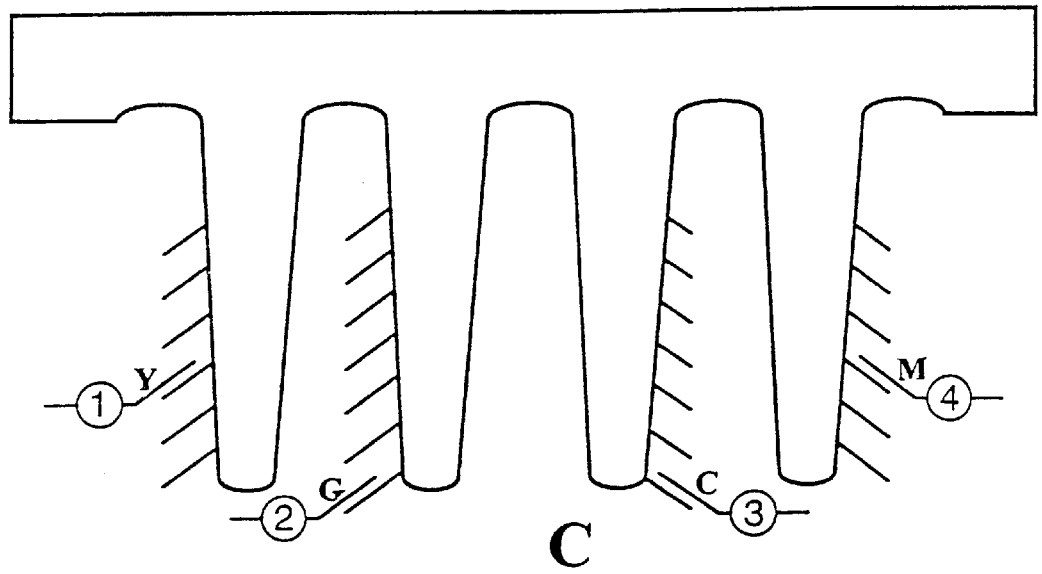

In another embodiment of the subject polynucleotide recovery devices, the solid support is a multiple projection electrophoresis loading device, such as a gel comb having a plurality of well-filling members, i.e., projections are well-filling members (FIG. 3C). The projections may be used to introduce polynucleotides into electrophoresis gels. Each well-filling projection comprises at least one recovery tag binding compound attached to the surface of the projection in such a way so as to permit the recovery binding tag compounds to bind to the recovery binding tags. The well-filling projections may have the same or different recovery tag binding compounds. Thus, by contacting a reaction mixture comprising a plurality of sequencing ladders or polynucleotide amplification products synthesized from recoverable primers with the projections of a multiple projection electrophoresis loading device of the invention, the different sequencing ladders or amplification products may be separated, purified, and immobilized on the different projections. The multiple projection electrophoresis loading devices of the invention may comprise one or more flexible regions so as to conform the shape of the device to that of the projections. In other embodiments of the multiple projection electrophoresis loading devices of the invention, the projections are positioned so as to be in register with wells (or other fluid receptacles) in which the primer extension reactions are carried out. For example, when sequencing reactions are performed in the wells of 96 well (8 by 12) microtiter plates, multiple projection electrophoresis loading devices with 96 projections in an 8 by 12 array may be used to remove the polynucleotide reaction products from the well and transfer them to an electrophoretic separation device.

Other embodiments of the subject polynucleotide recovery devices include sets of two or more easily manipulated solid support units, such as macroscopic beads, wherein each unit has one or more recovery tag binding compounds. In embodiments of these unit sets having multiple different recovery tag binding compounds on the same unit, the different recovery tag binding compounds may or may not be segregated from each other. The units may have identifying labels (e.g., colors, numbers, or labels). The individual units of a set may be joined to each other so at to provide for the convenient manipulation of each member of the set. The units may be joined to each other by a flexible connector, such a connector may be conveniently broken after the solid supports are removed from the solution (or solutions) containing the recovery tags. For example, the polynucleotide recovery device may take the form of macroscopic beads joined to one another on a flexible "string", wherein each bead (other than the terminal beads) is joined to two other beads by a flexible connector. Thus pulling one of the joined beads from a recovery tag containing solution would result in pulling of all of the beads from the solution. The connections between individual beads could be selectively severed, thereby providing for the controlled manipulation of the individual beads.

The invention also provides kits designed to expedite performing the subject methods. Kits serve to expedite the performance of the methods of interest by assembling two or more components required for carrying out the methods. Kits preferably contain components in pre-measured unit amounts, so as to minimize the need for measurements by end users of the kits. Kits preferably include instructions for performing one or more methods of the invention. Preferably, the components of kits are optimized so as to operate in conjunction with one another. The kits of the invention may be used to generate and/or separate a plurality of amplification products or sequencing ladders. The kits of the invention comprise a set of at least two primers adapted for generating a plurality of recoverable sequencing ladders or recoverable amplification products. Preferably, the primer sets in the subject kits are integrated sets of recoverable primers. The primers of the subject kit may be supplied separately or supplied in the same solution. The recoverable primers may or may not be labeled. Kits for generating a plurality of recoverable amplification products comprise at least two pairs of amplification primers, wherein at least one member of each pair is a recoverable primer. In addition to comprising recoverable primers, the subject kits may further comprise primer oligonucleotides that do not comprise a recovery tag. The subject kits for generating a plurality of recoverable sequencing ladders or recoverable amplification products may further comprise recovery tag binding compounds selected to specifically bind to the recovery tags (or functional equivalents thereof) present on the recoverable polynucleotide amplification products or recoverable sequencing ladders generated using the primers of the kit. The recovery tag binding compounds may be supplied in free solution or may be supplied immobilized to polynucleotide recovery devices. The kits of the invention may further comprise additional reagents required for polynucleotide sequencing or amplification. Such reagents include concentrated reaction buffers, dNTPs (all four bases in nucleotide triphosphate form), chain terminators (either dye labeled or not), and a thermostable DNA polymerase. The kits of the invention may further comprise polynucleotide recovery devices of the invention or solid supports that may be easily converted to polynucleotide recovery devices, e.g., well filling electrophoresis gel combs that have been coated with avidin.

The invention, having been described above, may be better understood by reference to the following examples. These examples are offered to illustrate the invention and should not be construed as limitations on the invention.

EXAMPLES

Experiment #1

Multiplex Primer Sequencing of Three Different Templates Using Template-Specific Primers.

Three different plasmids, namely pGEM, pCDNA II 1.9 and pBSK, were simultaneously sequenced using the dideoxy sequencing method (Sanger et al., 74 Proc. Natl. Acad. Sci. U.S.A. 5463, 1977).

The sequence generating protocol used was essentially as described in ABI PRISM Dye Primer Cycle Sequencing Core Kit, FS manual (PN402114), except that FAM-SP6, i.e., FAM labeled SP6 primer, (A,C, and G reactions) or ROX-SP6, i.e., ROX labeled SP6 primer, (T reaction) (specific for pGEM), JOE-25T(C), i.e., JOE labeled 25T(C) primer, specific for pCDNA II 1.9) and TAMRA KS (specific for pBSK) primers were all added to each of the A,C,G,T stock solutions. The primers sequences were as follows:

SP6: 5' ATTTAGGTGACACTATAG3' [SEQ ID NO: 1]

25T(C): 5' TTT TTT TTT TTT TTT TTT TTT TTT TC 3' [SEQ ID NO: 2]

KS: 5' CCT CGA GGT CGA CGG TAT CG 3' [SEQ ID NO: 3]

All templates (pGEM, pCDNA II 1.9 and pBSK) were added to each multiplex reaction, without otherwise modifying the sequencing chemistry. After cycling, A,C,G and T sequencing mixtures were not combined (as described in the protocol), but separately ethanol precipitated and electrophoretically analyzed on a sequencing gel using an ABI 373 DNA sequencer.

The results showed that in each of the A, C, G and T lanes all three one-color sequencing ladders were simultaneously detected. By selecting one color at a time and combining A, C G and T lanes across the gel good sequencing data were obtained for all templates, demonstrating that all three reactions occurred simultaneously with no apparent interference.

Experiment #2

Multiplex Terminator Sequencing Using 12 Different Tailed Sequencing Primers Targeting Five Different Templates, Followed by Sequential Selective Pull-Out of the Sequencing Ladders.

A multiplex sequencing reaction of five different templates was carried out, followed by selective hybridization based pull-out that uses a complementary capture sequence on a solid support.

Seven of the twelve primers (MC12-F2,-F3,-F4,-F5,-F6,-RC1,-RC2) were designed to target a contiguous region in the PCR product of a MC12 Blue Script vector (~3000 bp fragment that includes the whole insert), so that an overlap in the sequences of the sequencing extension products produced (~400 to 700 bases long) resulted. Another primer (5B5F5) targeted part of the insert of a 5B5 vector, whereas the remaining primers (MSH2-7,-12,-13,-15) were designed to sequence short PCR products (~200–500 bp) from human genomic DNA (Exons 7, 12, 13, 15 of the MSH2 gene). All templates were simultaneously sequenced using the dideoxy sequencing method (Sanger et al., 74 Proc. Natl. Acad. Sci U.S.A. 5463, 1977).

The protocol used was essentially as described in ABI PRISM Dye Terminator Cycle Sequencing Core Kit, FS manual (PN402116), except that the concentrations of sequencing reagents and cycle parameters were optimized to guarantee successful sequencing of all templates under the same conditions. Double the concentration of sequencing buffer (~80 mM) and three times the concentration of polymerase (~0.053 $\mu$M) and pyrophosphatase (3Units), dNTPs (~2.4 mM) and dye terminators (~1.2 mM) were used for a twelve-plex (i.e., 12 fold multiplex sequencing), as compared to the recommended concentrations for a single-plex reaction. The total magnesium concentration was ~7 mM, and the total volume of the reaction was 30 $\mu$l. The templates concentrations were ~0.013 $\mu$M for the MC12 PCR amplicon, ~0.02 $\mu$M for the 5B5 clone, and ~0.01 $\mu$M for each of the MSH2 PCR amplicons, respectively. The primers concentrations ranged from 0.05 to 0.17 $\mu$M, with a total concentration of ~1.2 $\mu$M. The number of cycles and the temperatures were (96° C. 5sec-53° C. 10sec-60° C. 4 min). 25 five cycles were performed. At the end of the cycles the tubes were heated at 99.9° C. for 8 min, to destroy all enzymatic activity.

Each of the sequencing primers (recoverable primers) was synthesized so as to have a unique six base DNA leader sequence, i.e., a balancing sequence, present on its 5' end. The balancing sequence did not hybridize to the sequencing template. The base composition of the twelve different six base leader sequences was designed so that the melting temperature would be similar for all the primer and complementary pull-out sequences. The pull-out complementary sequences (i.e., recovery tag binding compounds) were 15 bases long and designed to be complementary to the 6-mer leader sequence plus 9 bases of the annealing region located adjacent to the 6-mer. The pull-out oligos had a 3' biotin attached, so that they could be coupled to a solid support through biotin/streptavidin binding. Such a system allows to separate and easily manipulate the specifically hybridized sequencing extension products during hybridization, washing and elution steps.

The sequences of recoverable primers and recovery tag compounds were as follows:

| | |
|---|---|
| 1) MC12-F2: [SEQ ID NO:4] | 5' TTG GCT (tail) ACT TAG TGC ATA TTT TAA CGG TAC 3' (primer) [SEQ ID NO:4] |
| | 5' GCA CTA AGT AGC CAA 3' (capture sequence) [SEQ ID NO:5] |
| 2) MC12-F3: [SEQ ID NO:6] | 5' CTC TCT (tail) CCC AAG AGC AGT TAC ATT ACA AGG 3' (primer) |
| | 5' GCT CTT GGG AGA GAG 3' (capture sequence) [SEQ ID NO:7] |
| 3) MC12-F4: [SEQ ID NO:7] | 5' GGG TTT (tail) ATT CAG TGG TAC CCC TAC TCA GAG 3' (primer) |
| | 5' CCA CTG AAT AAA CCC 3' (capture sequence) [SEQ ID NO:8] |
| 4) MC12-F5: [SEQ ID NO:9] | 5' CCA CCT (tail) AAA TAA GCT TTA ATG TAA AAT ATG 3' (primer) [SEQ ID NO:9] |
| | 5' AGC TTA TTT AGG TGG 3' (capture sequence) [SEQ ID NO:10] |
| 5) MC12-F6: [SEQ ID NO:11] | 5' GAA GCT (tail) TCT TCT AAA AAG TAC TAA TGT TTG 3' (primer) [SEQ ID NO:11] |
| | 5' TTT AGA AGA AGC TTC 3' (capture sequence) [SEQ ID NO:12] |
| 6) MC12-RC1: [SEQ ID NO:13] | 5' AGA GAG (tail) TGT TAT AGA ATC TTC ATG GAC ATC 3' (primer) [SEQ ID NO:13] |
| | 5' ACT ATA ACA CTC TCT 3' (capture sequence) [SEQ ID NO:14] |
| 7) MC12-RC2: [SEQ ID NO:15] | 5' AAT TAA (tail) ATG GTC CTA GTT AAT AAA GAT CAC 3' (primer) |
| | 5' TAG GAC CAT TTA ATT 3' (capture sequence) [SEQ ID NO:16] |
| 8) 5B5-F5: [SEQ ID NO:17] | 5' ATC AGG (tail) TAA CAG TCA TCA TAT TCT GTA TGC 3' (primer) |
| | 5' TGA CTG TTA CCT GAT 3' (capture sequence) [SEQ ID NO:18] |
| 9) MSH-7: [SEQ ID NO:19] | 5' ATT AGA (tail) CGA CTT AGT TGA GAC TTA CGT GC 3' (primer) |
| | 5' ACT AAG TCG TCT AAT 3' (capture sequence) [SEQ ID NO:20] |
| 10) MSH-12: [SEQ ID NO:21] | 5' GAA GCA (tail) TCA GTA TTC CTG TGT ACA TTT 3' (primer) |
| | 5' GAA TAC TGA TGC TTC 3' (capture sequence) [SEQ ID NO:22] |
| 11) MSH-13: (primer) [SEQ ID NO:23] | 5' GCG ATA (tail) GTA GCA GAA AGA AGT TTA AAA CTT GC 3' (primer) [SEQ ID NO:23] |
| | 5' TTC TGC TAC TAT CGC 3' (capture sequence) [SEQ ID NO:24] |
| 12) MSH-15: [SEQ ID NO:25] | 5' AGA CAT (tail) TGC TGT CTC TTC TCA TGC TG 3' (primer) |
| | 5' GAG ACA GCA ATG TCT 3' (capture sequence) [SEQ ID NO:26] |

After carrying out the sequencing reaction, each of the twelve sequencing ladders was sequentially pulled-out of the mixture by means of selective hybridization. The hybridization step was carried out in the following way. First the solid support (streptavidin-coated silica beads) with the attached recovery tag binding compounds was pre-washed three times in 10 mM Tris, 1 mM EDTA, pH 8.0, 0.1% Tween 20; then once in 100 mM Tris, 1 mM EDTA, pH 8.0, 2 M NaCl, 0.1% Tween 20. The beads were then incubated with the multiplex sequencing reaction at 32° C. for 30 min. Once the coupling reaction was complete, the tube was briefly spun down to pellet the beads with the pull-out complex, and the sequencing reaction was transferred to the next hybridization tube. The beads with the pull-out complex were washed twice in 10 mM Tris, 1 mM EDTA, pH 8.0, 0.1% Tween 20; once in 70% ethanol; and vacuum-dried.

Prior to electrophoretic analysis, the hybridization-bound sequencing extension products were released in 2.5 μl of standard loading buffer (deionized formamide and dextran blue/EDTA mix 5:1) by heating at 60° C. for 4 min.

Good sequencing data were obtained for all targeted templates, indicating that all reactions had successfully occurred simultaneously and could be efficiently captured. The overall signals were sufficient to guarantee good accuracy up to approximately 600 bases. In the case of overlapping primers, the signal was found to decrease in intensity (while still providing redundant sequencing information) when the sequence reached the region of annealing of the subsequent primer. The very low background noise indicated the absence of non-specific binding.

Experiment #4
Multiplex PCR Purification Using Hinged PCR Primers.

As a model for the pull-out of a multiplexed PCR reaction, three individual PCR reactions were performed separately and then combined in one tube. One hinged primer was used in each of the three pairs of amplification primers. The reaction products were selectively purified using hybridization based pull-out specific for the recovery tag oligonucleotides on the hinged primers.

Three different PCR amplifications were done separately, using GeneAmp™ PCR Reagent Kit with AmpliTaq Gold™ DNA Polymerase (Perkin-Elmer, Norwalk, Conn., PN#N801-0055). The protocol used was essentially as described in the PCR kit manual, except that the concentration of PCR reagents and cycling parameters were optimized to facilitate successful amplification. PCR protocols were essentially as described in *PCR Protocols,* Michael A. Innis et al., 1990, Academic Press Inc., U.S. Pat. No. 4,683,195, and U.S. Pat. No. 4,683,202.

Standard PCR reaction conditions used were; 111 ng of Raji cell line DNA, 200 fMolar of forward and reverse primers, 100 nMolar dNTPs mix, 175nMolar $MgCl_2$, 1×Kit PCR buffer, 2.5 units of AmpliTaq Gold™ Polymerase and distilled water to bring the final reaction volume to 50 uls.

The PCR thermal profile used was; 95° C.-10 minute step to activate the AmpliTaq Gold™ enzyme, then 28 cycles of 97° C.-8 Seconds 59° C.-40 seconds 72° C.-72 seconds, the cycles were followed by a 99.9° C.-10 minute heating to inactivate the Taq Gold Enzyme and the last step, cooling the reaction to 4° C. for storage.

The three different PCR primer sets used were designed to amplify three distinct regions of human genomic DNA. The targeted MSH-2 regions of human genomic DNA were individually generated, producing short amplicon products (200–500 bp). One primer from each PCR primer set was a hinged recoverable primer having a 15 base oligonucleotide attached at its 3' end to the 5' end of the template specific PCR primer. The two oligonucleotides that constitute each hinged primer were physically linked together by a "non-DNA" linker unit(s) that could not be replicated by a DNA polymerase. The unique 15 base oligonucleotide attached to the PCR primers were not extendible and do not become template for the polymerase enzyme used to catalyze PCR ; thereby, leaving a portion of the primer single stranded and available to be captured, i.e. hybridized to the complementary 15 base oligonucleotide attached to a solid support.

PCR Primer Sets:
EXON7
Exon 7 Hinged Foward Primer:
5TTG GCT AGT TAG TGC3'-linker 5'CGA CTT AGT TGA GAC TTA CGT GC3'
Recovery Tag Sequence-linker-Forward Primer [SEQ ID NO:27]
Tag Binding Sequence:
5'GCACTAACTAGCCAA3' [SEQ ID NO:28]
Exon 7 Reverse Primer: 5'TTT ATG AGG ACA GCA CAT TGC3'
[SEQ ID NO:29]
EXON12
Exon 12 Hinged Foward Primer
5'GGG TTT ATT CAG TGG3'-linker 5'TCA GTA TTC CTG TGT ACA TTT3'
Recovery Tag Sequence-linker-Forward Primer:
[SEQ ID NO:30]
Tag Binding Sequence:
5'CCACTGAATAAACCC3'
[SEQ ID NO:31]
Exon 12 Reverse Primer:
5'TTA CCC CCA CAA AGC CCA A3'
[SEQ ID NO:32]
EXON13
Exon 13 Hinged Foward Primer:
5'CCA CCT AAATAAGCT3'-linker-5'GTAGCAGAAAGAAGTTTAAAACTT GC3'
Recovery Tag Sequence-linker-Forward Primer [SEQ ID NO:33]
Recovery Tag Binding Sequence:
5'AGCTTATTTAGGTGG3' [SEQ ID NO:34]
Exon 13 Reverse Primer:
5'GGACAGAGACATACATTTCTATCTTC3' [SEQ ID NO:35]

The amplification results were verified by agarose gel electrophoresis. The three different PCR amplicons reactions were mixed together. Beads comprising the complementary capture sequences (i.e., recovery tag binding compounds) were pre-washed in 1×TE and 0.1% Tween-20 solution twice, centrifuged to pellet the beads and remove wash liquid. The multiplex PCR mixture was added to the first set of capture beads in a tube and mixed. This reaction mixture was preheated to 80° C. for 2 minutes and then cool to 32° C. for a 30 minute incubation, to allow for the selective hybridization-based capture. The mixture was then centrifuged to pellet the beads. The solution was transferred to the next specific capture support tube and the hybridization reaction was repeated sequentially for each of the other amplicons. The beads having the bound amplicons were washed in 1×TE and 0.1% Tween-20 solution twice and once in 70% Ethanol, then vacuum dried in a speed vacuum. Upon elution from the support beads, captured amplicons were sequenced using the dideoxy sequencing method (Sanger et al., 74 Proc. Natl. Acad. Sci. U.S.A. 5463, 1977). Sequencing reactions were performed using an ABI PRISM™ Dye Terminator Cycle Sequencing Ready reaction kit (Perkin-Elmer, Norwalk Conn., PN#402078), using 2 pMoles of specific sequencing primer. The sequencing amplification thermal profile used was (96° C. 8 sec-53° C. 15sec-60° C. 4 minutes) for 25 cycles. Good sequencing data was obtained for all three targeted templates, indicating that the reaction had successfully been captured in sufficient concentration and purity from the multiplex PCR mixture of amplicons. The overall signals were sufficient to produce good accuracy. The low background noise indicated the absence of nonspecific binding from the capture. The individual PCR pullout products were also analyzed by gel electrophoresis prior to their use as templates for sequencing reactions, showing that indeed individual PCR products had been captured.

EQUIVALENTS

All publications and patent applications mentioned in this specification are indicative of the skill of those skilled in the art to which this invention pertains. All publications and patent applications are herein incorporated by reference to the same extent as if each individual publication or patent application was specifically and individually indicated to be incorporated by reference.

The foregoing written specification is considered to be sufficient to enable one skilled in the art to practice the invention. Indeed, various modifications of the above-described modes for carrying out the invention that are obvious to those skilled in the field of molecular biology or related fields are intended to be within the scope of the following claims.

What is claimed is:

1. A method of simultaneously generating a plurality of polynucleotide sequencing ladders, said method comprising, mixing a plurality of recoverable primers with a plurality of polynucleotide sequencing templates, generating a plurality of polynucleotide sequencing ladders, wherein each of the extension products is derived from one of the recoverable primers, and binding said polynucleotide sequencing ladders to recovery tag binding compounds, wherein the recovery tag binding compounds are immobilized in an addressable manner on one or more solid supports, whereby polynucleotide sequencing ladders are separated from one another.

2. A method according to claim 1, said method further comprising releasing the separated polynucleotide sequencing ladders from the solid supports, whereby a plurality of purified separated polynucleotide sequencing ladders is produced.

3. A method according to claim 2, wherein the recovery tags are oligonucleotides.

4. A method according to claim 3, wherein at least one of said recovery tags comprises a balancing polynucleotide sequence.

5. A method according to claim 2, wherein the generating of sequencing ladders comprises the step of adding a labeled chain terminator.

6. A method according to claim 2, wherein the recoverable primers are labeled.

7. A method according to claim 2, wherein the sequencing templates are located on the same polynucleotide.

8. A method according to claim 2, wherein the sequencing templates are located on different polynucleotides.

9. A method according to claim 2, wherein the recovery tag binding compounds are polynucleotides.

10. A method according to claim 2, wherein the solid support is a multiple-projection electrophoresis loading device.

11. A method according to claim 1, wherein the solid support is a plurality of beads.

12. A method according to claim 1, wherein the solid support is a multi-chamber liquid holding device.

13. A method according to claim 2, wherein each sequencing template is produced by a polynucleotide amplification reaction.

14. A method according to claim 13, wherein the polynucleotide amplification reaction is PCR.

15. A method according to claim 2, wherein the polynucleotide sequencing ladders are formed by cycle sequencing.

16. A method according to claim 2, wherein the polynucleotide sequencing ladders are generated by a sequence generation technique other than cycle sequencing.

17. A method according to claim 2, wherein the recovery tag binding compounds are polynucleotides complementary to polynucleotides synthesized during the generation of the polynucleotide sequencing ladders.

* * * * *

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single (D) TOPOLOGY: linear (xi) SEQUENCE DESCRIPTION: SEQ ID NO:1:

ATTTAGGTGA CACTATAG                                                 18

(2) INFORMATION FOR SEQ ID NO:2:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (xi) SEQUENCE DESCRIPTION: SEQ ID NO:2:

TTTTTTTTTT TTTTTTTTTT TTTTTC                                        26

(2) INFORMATION FOR SEQ ID NO:3:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (xi) SEQUENCE DESCRIPTION: SEQ ID NO:3:

CCTCGAGGTC GACGGTATCG                                               20

(2) INFORMATION FOR SEQ ID NO:4:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:4:

TTGGCTACTT AGTGCATATT TTAACGGTAC                                    30

(2) INFORMATION FOR SEQ ID NO:5:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:5:

GCACTAAGTA GCCAA                                                    15

(2) INFORMATION FOR SEQ ID NO:6:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:6:

CTCTCTCCCA AGAGCAGTTA CATTACAAGG                                    30

(2) INFORMATION FOR SEQ ID NO:7:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:7:

GCTCTTGGGA GAGAG                                                            15

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:8:

CCACTGAATA AACCC                                                            15

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:9:

CCACCTAAAT AAGCTTTAAT GTAAAATATG                                            30

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:10:

AGCTTATTTA GGTGG                                                            15

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:11:

GAAGCTTCTT CTAAAAAGTA CTAATGTTTG                                            30

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:12:

TTTAGAAGAA GCTTC                                                            15

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:13:

AGAGAGTGTT ATAGAATCTT CATGGACATC          30

(2) INFORMATION FOR SEQ ID NO:14:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:14:

ACTATAACAC TCTCT          15

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:15:

AATTAAATGG TCCTAGTTAA TAAAGATCAC          30

(2) INFORMATION FOR SEQ ID NO:16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:16:

TAGGACCATT TAATT          15

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:17:

ATCAGGTAAC AGTCATCATA TTCTGTATGC          30

(2) INFORMATION FOR SEQ ID NO:18:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:18:

TGACTGTTAC CTGAT          15

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:19:

ATTAGACGAC TTAGTTGAGA CTTACGTGC                                              29

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:20:

ACTAAGTCGT CTAAT                                                             15

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:21:

GAAGCATCAG TATTCCTGTG TACATTT                                                27

(2) INFORMATION FOR SEQ ID NO:22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:22:

GAATACTGAT GCTTC                                                             15

(2) INFORMATION FOR SEQ ID NO:23:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:23:

GCGATAGTAG CAGAAAGAAG TTTAAAACTT GC                                          32

(2) INFORMATION FOR SEQ ID NO:24:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:24:

TTCTGCTACT ATCGC                                                             15

(2) INFORMATION FOR SEQ ID NO:25:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:25:

```
AGACATTGCT GTCTCTTCTC ATGCTG                                                    26

(2) INFORMATION FOR SEQ ID NO:26:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (xi) SEQUENCE DESCRIPTION: SEQ ID NO:26:

GAGACAGCAA TGTCT                                                                15

(2) INFORMATION FOR SEQ ID NO:27:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (xi) SEQUENCE DESCRIPTION: SEQ ID NO:27:

TTGGCTAGTT AGTGCCGACT TAGTTGAGAC TTACGTGC                                       38

(2) INFORMATION FOR SEQ ID NO:28:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (xi) SEQUENCE DESCRIPTION: SEQ ID NO:28:

GCACTAACTA GCCAA                                                                15

(2) INFORMATION FOR SEQ ID NO:29:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO:29:

TTTATGAGGA CAGCACATTG C                                                         21

(2) INFORMATION FOR SEQ ID NO:30:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (xi) SEQUENCE DESCRIPTION: SEQ ID NO:30:

GGGTTTATTC AGTGGTCAGT ATTCCTGTGT ACATTT                                         36

(2) INFORMATION FOR SEQ ID NO:31:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (xi) SEQUENCE DESCRIPTION: SEQ ID NO:31:

CCACTGAATA AACCC                                                                15
```

(2) INFORMATION FOR SEQ ID NO:32:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:32:

TTACCCCCAC AAAGCCCAA                                              19

(2) INFORMATION FOR SEQ ID NO:33:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:33:

CCACCTAAAT AAGCTGTAGC AGAAAGAAGT TTAAAACTTG C                     41

(2) INFORMATION FOR SEQ ID NO:34:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:34:

AGCTTATTTA GGTGG                                                  15

(2) INFORMATION FOR SEQ ID NO:35:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:35:

GGACAGAGAC ATACATTTCT ATCTTC                                      26

(2) INFORMATION FOR SEQ ID NO:36:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:36:

TAATATATTA TATAATATAT CGATTA                                      26

(2) INFORMATION FOR SEQ ID NO:37:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:37:

GTACATGGTA GCAATG                                                 16

(2) INFORMATION FOR SEQ ID NO:38:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:38:

```
AACTGTCCAT GTACCATCGT TACTGCCATA ATCTCGGATC                40
```

(2) INFORMATION FOR SEQ ID NO:39:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:39:

```
TAAATTTAAT ATATCGATTA CATGTACCAT C                         31
```

(2) INFORMATION FOR SEQ ID NO:40:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:40:

```
GTACATGGTA GCAATG                                          16
```

(2) INFORMATION FOR SEQ ID NO:41:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:41:

```
AACTGTCCAT GTACCATCGT TACTGCCATA ATCTCGGATC                40
```

(2) INFORMATION FOR SEQ ID NO:42:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:42:

```
ATGTACCATC GTTACTGCCA TAA                                  23
```

(2) INFORMATION FOR SEQ ID NO:43:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:43:

```
TACATGGTAG CAATGACGGT ATT                                  23
```

(2) INFORMATION FOR SEQ ID NO:44:

(i) SEQUENCE CHARACTERISTICS:
  (A) LENGTH: 40 base pairs
  (B) TYPE: nucleic acid
  (C) STRANDEDNESS: single
  (D) TOPOLOGY: linear (xi) SEQUENCE DESCRIPTION: SEQ ID NO:44:

AACTGTCCAT GTACCATCGT TACTGCCATA ATCTCGGATC     40

(2) INFORMATION FOR SEQ ID NO:45:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (xi) SEQUENCE DESCRIPTION: SEQ ID NO:45:

TACCATCGTT ACTGCCATAA TC     22

(2) INFORMATION FOR SEQ ID NO:46:

(i) SEQUENCE CHARACTERISTICS:
  (A) LENGTH: 40 base pairs
  (B) TYPE: nucleic acid
  (C) STRANDEDNESS: single
  (D) TOPOLOGY: linear (xi) SEQUENCE DESCRIPTION: SEQ ID NO:46:

TTGACAGGTA CATGGTAGCA ATGACGGTAT TAGAGCCTAG     40

(2) INFORMATION FOR SEQ ID NO:47:

(i) SEQUENCE CHARACTERISTICS:
  (A) LENGTH: 40 base pairs
  (B) TYPE: nucleic acid
  (C) STRANDEDNESS: single
  (D) TOPOLOGY: linear (xi) SEQUENCE DESCRIPTION: SEQ ID NO:47:

AACTGTCCAT GTACCATCGT TACTGCCATA ATCTCGGATC     40

(2) INFORMATION FOR SEQ ID NO:48:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (xi) SEQUENCE DESCRIPTION: SEQ ID NO:48:

GTTACTGCCA TAATCTCGGA TC     22

(2) INFORMATION FOR SEQ ID NO:49:

(i) SEQUENCE CHARACTERISTICS:
  (A) LENGTH: 40 base pairs
  (B) TYPE: nucleic acid
  (C) STRANDEDNESS: single
  (D) TOPOLOGY: linear (xi) SEQUENCE DESCRIPTION: SEQ ID NO:49:

TTGACAGGTA CATGGTAGCA ATGACGGTAT TAGAGCCTAG     40

(2) INFORMATION FOR SEQ ID NO:50:

-continued

```
    (i) SEQUENCE CHARACTERISTICS:
          (A) LENGTH: 40 base pairs
          (B) TYPE: nucleic acid
          (C) STRANDEDNESS: single
          (D) TOPOLOGY: linear (xi) SEQUENCE DESCRIPTION: SEQ ID NO:50:

AACTGTCCAT GTACCATCGT TACTGCCATA ATCTCGGATC                              40
```